(12) United States Patent
Lee et al.

(10) Patent No.: US 11,648,064 B2
(45) Date of Patent: *May 16, 2023

(54) MOTORIZED FULL FIELD ADAPTIVE MICROSCOPE

(71) Applicant: SYNAPTIVE MEDICAL INC., Toronto (CA)

(72) Inventors: Tammy Kee-Wai Lee, Toronto (CA); Michael Frank Gunter Wood, Toronto (CA); Cameron Anthony Piron, Toronto (CA); Brent Andrew Bailey, Toronto (CA); Sagar Saxena, Mississauga (CA); Sean Adrian Conroy, Toronto (CA); Kamyar Abhari, Toronto (CA); Kai Michael Hynna, Toronto (CA); Gal Sela, Toronto (CA); Kelly Noel Dyer, Toronto (CA); Joshua Lee Richmond, Toronto (CA)

(73) Assignee: Synaptive Medical Inc.

( * ) Notice: Subject to any disclaimer, the term of this patent is extended or adjusted under 35 U.S.C. 154(b) by 0 days.

This patent is subject to a terminal disclaimer.

(21) Appl. No.: 17/805,771

(22) Filed: Jun. 7, 2022

(65) Prior Publication Data

US 2022/0296314 A1    Sep. 22, 2022

Related U.S. Application Data

(63) Continuation of application No. 17/103,015, filed on Nov. 24, 2020, now Pat. No. 11,376,081, which is a
(Continued)

(51) Int. Cl.
*A61B 34/20* (2016.01)
*G02B 21/00* (2006.01)
(Continued)

(52) U.S. Cl.
CPC .............. *A61B 34/20* (2016.02); *A61B 90/20* (2016.02); *A61B 90/25* (2016.02); *A61B 90/30* (2016.02);
(Continued)

(58) Field of Classification Search
None
See application file for complete search history.

(56) References Cited

U.S. PATENT DOCUMENTS 10,925,675 B2 * 2/2021 Lee .................. G02B 21/025
11,376,081 B2 * 7/2022 Lee .................. A61B 90/25
(Continued)

OTHER PUBLICATIONS

Tammy Kee-Wai Lee et al., "Motorized Full Field Adaptive Microscope", U.S. Appl. No. 15/570,904, filed Oct. 31, 2017, now U.S. Pat. No. 10,925,675, issued Feb. 23, 2021.
(Continued)

*Primary Examiner* — Kaitlin A Retallick

(57) ABSTRACT

An optical imaging system for imaging a target during a medical procedure, the imaging system involving an optical assembly having moveable zoom optics and moveable focus optics, a zoom actuator and a focus actuator for positioning the zoom and focus optics, respectively, a controller for controlling the zoom and focus actuators independently in response to received control input, a camera for capturing an image of the target from the optical assembly, the system capable of performing autofocus during a medical procedure.

19 Claims, 14 Drawing Sheets

Related U.S. Application Data continuation of application No. 15/570,904, filed as application No. PCT/CA2015/050948 on Sep. 24, 2015, now Pat. No. 10,925,675.

(51) Int. Cl.

| | | |
|---|---|---|
| *A61B 90/25* | (2016.01) | |
| *A61B 90/30* | (2016.01) | |
| *G02B 21/08* | (2006.01) | |
| *A61B 90/20* | (2016.01) | |
| *G02B 21/36* | (2006.01) | |
| *A61B 90/00* | (2016.01) | |
| *G02B 7/09* | (2021.01) | |
| *G02B 21/02* | (2006.01) | |
| *G02B 21/06* | (2006.01) | |
| *H04N 5/232* | (2006.01) | |
| *G06T 19/00* | (2011.01) | |

(52) U.S. Cl.
CPC ............ *A61B 90/361* (2016.02); *A61B 90/37* (2016.02); *G02B 7/09* (2013.01); *G02B 21/0012* (2013.01); *G02B 21/025* (2013.01); *G02B 21/06* (2013.01); *G02B 21/084* (2013.01); *G02B 21/362* (2013.01); *G02B 21/365* (2013.01); *G02B 21/368* (2013.01); *H04N 5/23203* (2013.01); *H04N 5/23216* (2013.01); *H04N 5/23296* (2013.01); *A61B 2034/2051* (2016.02); *A61B 2034/2055* (2016.02); *A61B 2034/2057* (2016.02); *A61B 2090/367* (2016.02); *A61B 2090/373* (2016.02); *G06T 19/006* (2013.01)

(56) References Cited

U.S. PATENT DOCUMENTS

| | | | | |
|---|---|---|---|---|
| 2009/0128926 | A1* | 5/2009 | Perreault | G02B 7/102 359/698 |
| 2010/0097498 | A1* | 4/2010 | Zaifrani | G02B 7/102 348/240.99 |
| 2014/0005484 | A1* | 1/2014 | Charles | A61B 34/20 600/201 |
| 2016/0205358 | A1* | 7/2016 | Dickinson | H04N 7/188 348/157 |

OTHER PUBLICATIONS

Tammy Kee-Wai Lee et al., "Motorized Full Field Adaptive Microscope", U.S. Appl. No. 17/103,015, filed Nov. 24, 2020, Notice of Allowance issued.

* cited by examiner

MOTORIZED FULL FIELD ADAPTIVE MICROSCOPE

CROSS-REFERENCE TO RELATED APPLICATION(S)

This document is a continuation application claiming the benefit of, and priority to, U.S. patent application Ser. No. 17/103,015, filed on Nov. 24, 2020, entitled "MOTORIZED FULL FIELD ADAPTIVE MICROSCOPE," U.S. patent application Ser. No. 15/570,904, filed on Oct. 31, 2017, entitled "MOTORIZED FULL FIELD ADAPTIVE MICROSCOPE," and International Application No. PCT/CA2015/050948, filed on Sep. 24, 2015, and entitled "MOTORIZED FULL FIELD ADAPTIVE MICROSCOPE," all of which are hereby incorporated by reference herein in their entirety.

FIELD

The present disclosure generally relates to optical imaging systems, including optical imaging systems suitable for use in image guided medical procedures.

BACKGROUND

Surgical microscopes are often used during surgical procedures to provide a detailed or magnified view of the surgical site. In some cases, separate narrow field and wide field scopes may be used within the same surgical procedure to obtain image views with different zoom ranges. Often, adjusting the zoom and focus of such a surgical microscope require the user, e.g., a surgeon, to manually adjust the optics of the microscope, which may be difficult, time-consuming and frustrating, particularly during a surgical procedure. As well, image capture cameras and light sources often are separate pieces of equipment from the surgical microscope, such that the specific camera and light source used with a given surgical microscope may be different for different medical centers and even for different surgical procedures within the same medical center. This may result in an inconsistency in the images obtained, which may make it difficult or impossible to compare images between different medical centers.

SUMMARY

In some examples, the present disclosure provides an optical imaging system for imaging a target during a medical procedure. The system includes: an optical assembly including moveable zoom optics and moveable focus optics; a zoom actuator for positioning the zoom optics; a focus actuator for positioning the focus optics; a controller for controlling the zoom actuator and the focus actuator in response to received control input; and a camera for capturing an image of the target from the optical assembly, wherein the zoom optics and the focus optics are independently moveable by the controller using the zoom actuator and the focus actuator, respectively, and wherein the optical imaging system is configured to operate at a minimum working distance from the target, the working distance being defined between an aperture of the optical assembly and the target.

In some examples, the present disclosure provides a processor for controlling the optical imaging system disclosed herein. The processor is configured to: provide a user interface to receive control input, via an input device coupled to the processor, for controlling the zoom actuator and the focus actuator; transmit control instructions to the controller of the optical imaging system to adjust zoom and focus in accordance with the control input; and receive image data from the camera for outputting to an output device coupled to the processor.

In some examples, the present disclosure provides a system for optical imaging during a medical procedure. The system comprises: the optical imaging system disclosed herein; a positioning system for positioning the optical imaging system; and a navigation system for tracking each of the optical imaging system and the positioning system relative to the target.

In some examples, the present disclosure provides a method of autofocusing using an optical imaging system during a medical procedure, the optical imaging system including motorized focus optics and a controller for positioning the focus optics. The method comprises: determining a working distance between an imaging target and an aperture of the optical imaging system; determining a desired position of the focus optics based on the working distance; and positioning the focus optics at the desired position.

BRIEF DESCRIPTIONS OF THE DRAWINGS

Reference will now be made, by way of example, to the several figures of the accompanying drawings which show example embodiments of the present disclosure, and in which.

Similar reference numerals may have been used in different figures to denote similar components.

DETAILED DESCRIPTION

Figure 1:
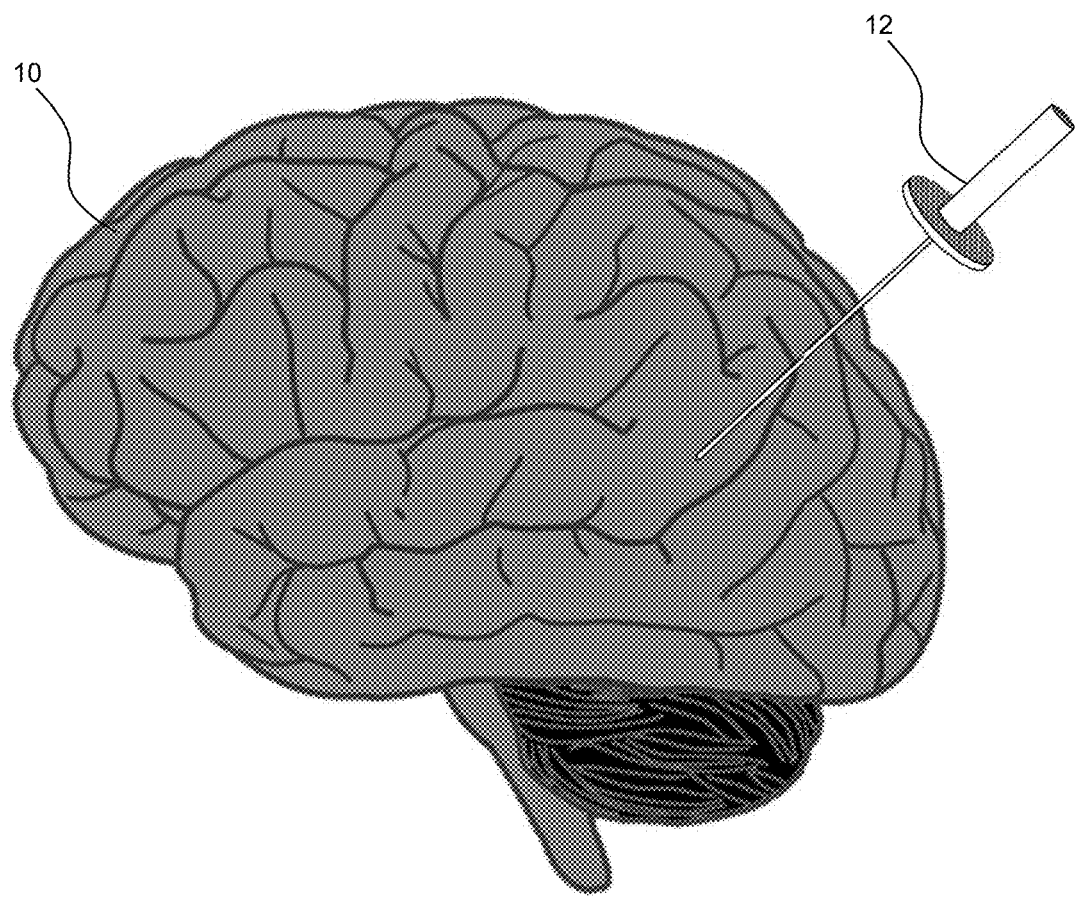
FIG. 1 is a diagram illustrating the insertion of an access port into a human brain, for providing access to internal brain tissue during an example medical procedure.

The systems and methods described herein may be useful in the field of neurosurgery, including oncological care, neurodegenerative disease, stroke, brain trauma, and orthopedic surgery. The teachings of the present disclosure may be applicable to other conditions or fields of medicine. While the present disclosure describes examples in the context of neurosurgery, the embodiment of the present disclosure may be applicable to other surgical procedures that may use intraoperative optical imaging.

Various example apparatuses or processes are below described. No example embodiment described herein limits any claimed embodiment and any claimed embodiments may cover processes or apparatuses that differ from those examples below described. The claimed embodiments are not limited to apparatuses or processes having all of the features of any one apparatus or process described below or to features common to multiple or all of the apparatuses or processes below described. It is possible that an apparatus or process described below is not part of any claimed embodiment.

Furthermore, numerous specific details are set forth in order to provide a thorough understanding of the disclosure. However, the embodiments described herein may be practiced without these specific details. In other instances, well-known methods, procedures, and components have not been described in detail so as not to obscure the embodiments described herein.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" or "example" means "serving as an example, instance, or illustration," and should not be construed as preferred or advantageous over other configurations disclosed herein.

As used herein, the terms "about", "approximately", and "substantially" are meant to cover variations that may exist in the upper and lower limits of the ranges of values, such as variations in properties, parameters, and dimensions. In one non-limiting example, the terms "about", "approximately", and "substantially" may be understood to mean plus or minus 10 percent or less.

Unless defined otherwise, all technical and scientific terms used herein are intended to have the same meaning as commonly understood by one of ordinary skill in the art. Unless otherwise indicated, such as through context, as used herein, the following terms are intended to have the following meanings:

As used herein, the phrase "access port" refers to a cannula, conduit, sheath, port, tube, or other structure that is insertable into a subject, in order to provide access to internal tissue, organs, or other biological substances. In some embodiments, an access port may directly expose internal tissue, for example, via an opening or aperture at a distal end thereof, and/or via an opening or aperture at an intermediate location along a length thereof. In other embodiments, an access port may provide indirect access, via one or more surfaces that are transparent, or partially transparent, to one or more forms of energy or radiation, such as, but not limited to, electromagnetic waves and acoustic waves.

As used herein the phrase "intraoperative" refers to an action, process, method, event or step that occurs or is carried out during at least a portion of a medical procedure. Intraoperative, as defined herein, is not limited to surgical procedures, and may refer to other types of medical procedures, such as diagnostic and therapeutic procedures.

Some embodiments of the present disclosure relate to minimally invasive medical procedures that are performed via an access port, whereby surgery, diagnostic imaging, therapy, or other medical procedures, e.g., minimally invasive medical procedures, are performed based on access to internal tissue through the access port.

In the example of a port-based surgery, a surgeon or robotic surgical system may perform a surgical procedure involving tumor resection in which the residual tumor remaining after is minimized, while also minimizing the trauma to the intact white and grey matter of the brain. In such procedures, trauma may occur, for example, due to contact with the access port, stress to the brain matter, unintentional impact with surgical devices, and/or accidental resection of healthy tissue. A key to minimizing trauma is ensuring that the surgeon performing the procedure has the best possible view of the surgical site of interest without having to spend excessive amounts of time and concentration repositioning tools, scopes and/or cameras during the medical procedure.

Referring to FIG. 1, this diagram illustrates the insertion of an access port 12 into a human brain 10, for providing access to internal brain tissue during a medical procedure. The access port 12 is inserted into the human brain 10, providing access to internal brain tissue. The access port 12 comprises such instruments as catheters, surgical probes, or cylindrical ports such as the NICO BRAINPATH™. Surgical tools and instruments can be inserted within the lumen of the access port 12 in order to perform surgical, diagnostic, or therapeutic procedures, such as resecting tumors as necessary. In the example of a port-based surgery, a straight or linear access port 12 is typically guided down a sulci path of the brain. Surgical instruments would then be inserted down the access port 12. The embodiments of the present disclosure apply equally well to catheters, DBS needles, a biopsy procedure, and also to biopsies and/or catheters in other medical procedures performed on other parts of the body, as well as to medical procedures that do not use an access port. Various examples of embodiments of the present disclosure are generally suitable for use in any medical procedure using optical imaging systems.

Figure 2A:
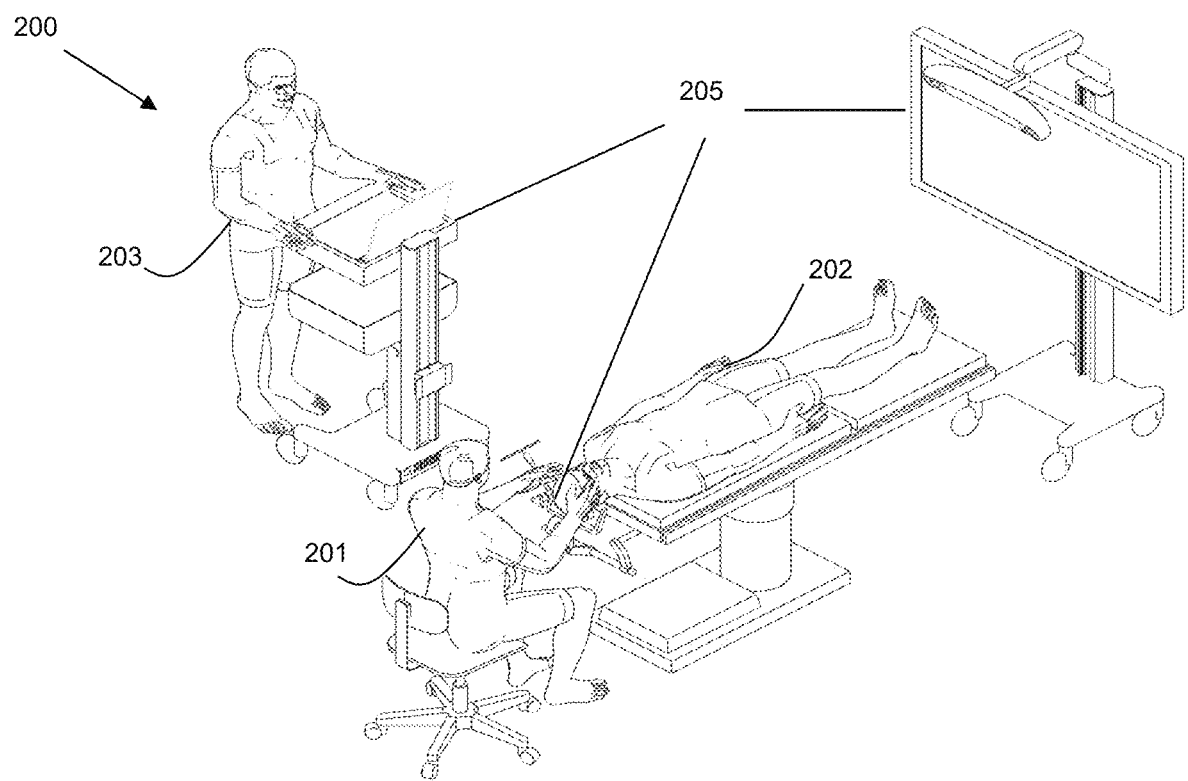
FIG. 2A is a diagram illustrating an example navigation system to support image guided surgery.

Referring to FIG. 2A, this diagram illustrates an exemplary navigation system environment 200 which may be used to support navigated image-guided surgery. A surgeon 201 conducts a surgery on a patient 202 in an operating room (OR) environment. A medical navigation system 205 comprises an equipment tower, tracking system, displays and tracked instruments to assist the surgeon 201 during his procedure. An operator 203 may also be present to operate, control, and provide assistance for the medical navigation system 205.

Figure 2B:
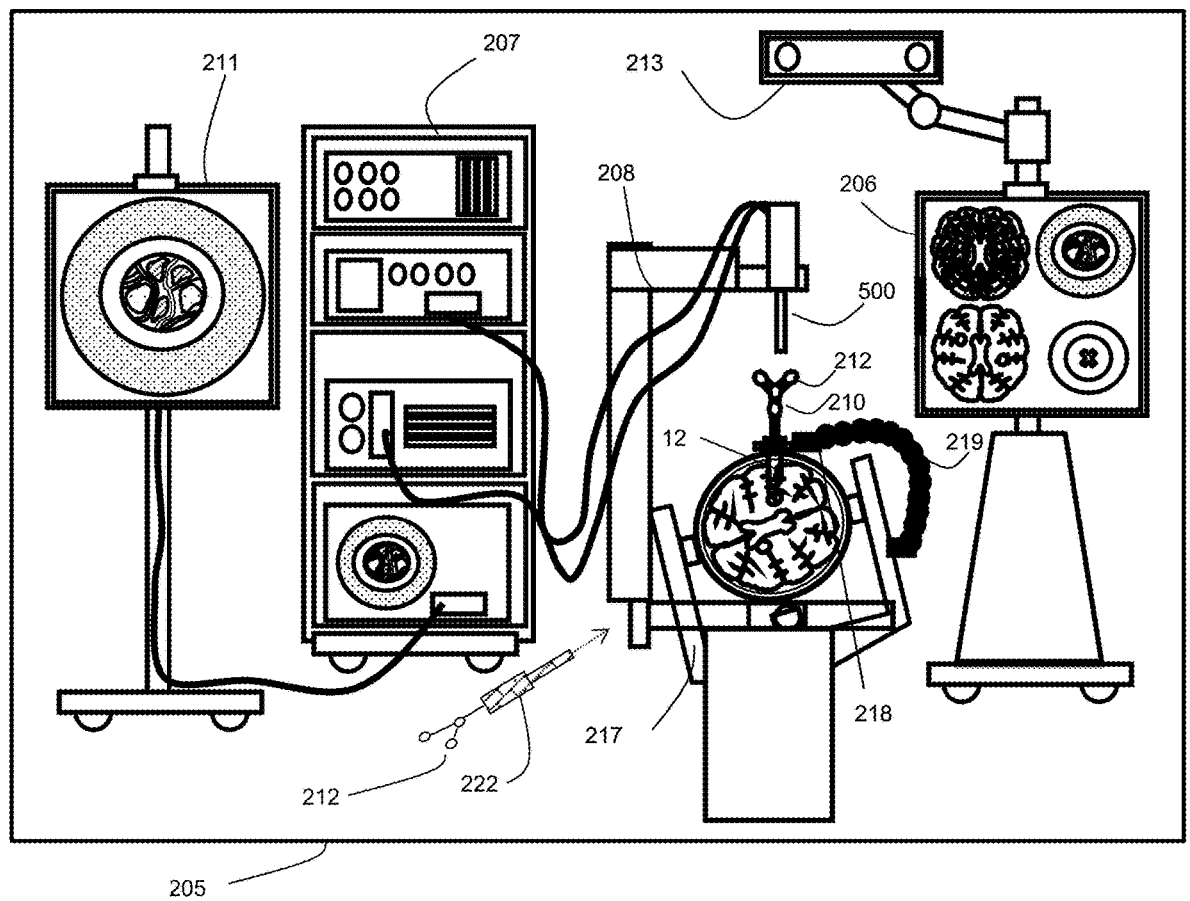
FIG. 2B is a diagram illustrating system components of an example navigation system.

Referring to FIG. 2B, this diagram illustrates an example medical navigation system 205 in greater detail. The disclosed optical imaging system may be used in the context of the medical navigation system 205. The medical navigation system 205 may include one or more displays 206, 211 for displaying a video image, an equipment tower 207, and a positioning system 208, such as a mechanical arm, which may support an optical imaging system 500 (which may include an optical scope). One or more of the displays 206, 211 may include a touch-sensitive display for receiving touch input. The equipment tower 207 may be mounted on a frame, e.g., a rack or cart, and may contain a power supply and a computer or controller that may execute planning software, navigation software and/or other software to manage the positioning system 208 one or more instruments tracked by the navigation system 205. In some examples of the medical navigation system 205, the equipment tower 207 comprises a single tower configuration, operating with dual displays 206, 211; however, the equipment tower 207 also comprises other configurations, e.g., dual tower, single display, etc. The equipment tower 207 further comprises a universal power supply (UPS) to provide for emergency power, in addition to a regular AC adapter power supply.

Still referring to FIG. 2B, a portion of the patient's anatomy may be held in place by a holder. For example, as shown the patient's head and brain may be held in place by a head holder 217. An access port 12 and associated introducer 210 may be inserted into the head, to provide access to a surgical site in the head. The imaging system 500 may be used to view down the access port 12 at a sufficient magnification to allow for enhanced visibility down the access port 12. The output of the imaging system 500 may be received by one or more computers or controllers to generate a view that may be depicted on a visual display, e.g., one or more displays 206, 211.

Still referring to FIG. 2B, in some examples, the navigation system 205 may include a tracked pointer 222. The tracked pointer 222, comprises markers 212 to enable tracking by a tracking camera 213, is used to identify point, e.g., fiducial points, on a patient. An operator, typically a nurse or the surgeon 201, uses the tracked pointer 222 to identify the location of points on the patient 202, in order to register the location of selected points on the patient 202 in the navigation system 205. A guided robotic system with a closed loop control is usable as a proxy for human interaction. Guidance to the robotic system is provided by any combination of input sources, such as image analysis, tracking of objects in the operating room using markers placed on various objects of interest, or any other suitable robotic system guidance technique.

Still referring to FIG. 2B, fiducial markers 212 are coupled with the introducer 210 for tracking by the tracking camera 213, which provides positional information of the introducer 210 from the navigation system 205. In some examples, the fiducial markers 212 may be alternatively or additionally coupled with the access port 12. In some examples, the tracking camera 213 comprises a 3D infrared optical tracking stereo camera similar, such as a NORTHERN DIGITAL IMAGING® (NDI) device. In some examples, the tracking camera 213 comprises an electromagnetic system (not shown), such as a field transmitter that may use at least one more receiver coil disposed in relation to at least one tool that is to be tracked. A known profile of the electromagnetic field and known position of receiver coil(s) relative to each other may be used to infer the location of the tracked tool(s) using the induced signals and their phases in each of the receiver coils. Operation and examples of this technology is further explained in Chapter 2 of "Image-Guided Interventions Technology and Application," Peters, T.; Cleary, K., 2008, ISBN: 978-0-387-72856-7, incorporated herein by reference. Location data of the positioning system 208 and/or access port 12 may be determined by the tracking camera 213 by detection of the fiducial markers 212 placed on or otherwise in fixed relation, e.g., in rigid connection, to any of the positioning system 208, the access port 12, the introducer 210, the tracked pointer 222 and/or other tracked instruments. The fiducial marker(s) 212 may be active or passive markers. A display 206, 211 may provide an output of the computed data of the navigation system 205. In some examples, the output provided by the display 206, 211 may include axial, sagittal and coronal views of patient anatomy as part of a multi-view output.

Still referring to FIG. 2B, the active or passive fiducial markers 212 may be placed on tools, e.g., the access port 12 and/or the imaging system 500, to be tracked, to determine the location and orientation of these tools using the tracking camera 213 and navigation system 205. The markers 212 may be captured by a stereo camera of the tracking system to give identifiable points for tracking the tools. A tracked tool may be defined by a grouping of markers 212, which may define a rigid body to the tracking system. This may in turn be used to determine the position and/or orientation in 3D of a tracked tool in a virtual space. The position and orientation of the tracked tool in 3D may be tracked in six degrees of freedom, e.g., x, y, z coordinates and pitch, yaw, roll rotations, in five degrees of freedom, e.g., x, y, z, coordinate and two degrees of free rotation, but preferably tracked in at least three degrees of freedom, e.g., tracking the position of the tip of a tool in at least x, y, z coordinates. In typical use with navigation systems, at least three markers 212 are provided on a tracked tool to define the tool in virtual space, however, it is known to be advantageous for four or more markers 212 to be used.

Still referring to FIG. 2B, camera images capturing the markers 212 may be logged and tracked, by, for example, a closed circuit television (CCTV) camera. The markers 212 may be selected to enable or assist in segmentation in the captured images. For example, infrared (IR)-reflecting markers and an IR light source from the direction of the camera may be used. An example of such an apparatus may be tracking devices such as the POLARIS® system available from Northern Digital Inc. In some examples, the spatial position and orientation of the tracked tool and/or the actual and desired position and orientation of the positioning system 208 may be determined by optical detection using a camera. The optical detection may be done using an optical camera, rendering the markers 212 optically visible.

Still referring to FIG. 2B, in some examples, the markers 212, e.g., reflectospheres, may be used in combination with a suitable tracking system, to determine the spatial positioning position of the tracked tools within the operating theatre. Different tools and/or targets may be provided with respect to sets of markers 212 in different configurations. Differentiation of the different tools and/or targets and their corresponding virtual volumes may be possible based on the specification configuration and/or orientation of the different sets of markers 212 relative to one another, enabling each such tool and/or target to have a distinct individual identity within the navigation system 205. The individual identifiers may provide information to the system, such as information relating to the size and/or shape of the tool within the system. The identifier may also provide additional information such as the tool's central point or the tool's central axis, among other information. The virtual tool may also be determinable from a database of tools stored in or provided to the navigation system 205. The markers 212 may be tracked relative to a reference point or reference object in the operating room, such as the patient 202.

Still referring to FIG. 2B, various types of markers may be used. The markers 212 may all be the same type or may include a combination of two or more different types. Possible types of markers that could be used may include reflective markers, radiofrequency (RF) markers, electromagnetic (EM) markers, pulsed or un-pulsed light-emitting diode (LED) markers, glass markers, reflective adhesives, or reflective unique structures or patterns, among others. RF and EM markers may have specific signatures for the specific tools they may be attached to. Reflective adhesives, structures and patterns, glass markers, and LED markers may be detectable using optical detectors, while RF and EM markers may be detectable using antennas. Different marker types may be selected to suit different operating conditions. For example, using EM and RF markers may enable tracking of tools without requiring a line-of-sight from a tracking camera to the markers 212, and using an optical tracking system may avoid additional noise from electrical emission and detection systems.

Still referring to FIG. 2B, in some examples, the markers 212 may include printed or 3D designs that may be used for detection by an auxiliary camera, such as a wide-field camera (not shown) and/or the imaging system 500. Printed markers are used as a calibration pattern, for example, to provide distance information, e.g., 3D distance information, to an optical detector. Printed identification markers comprise configurations, such as concentric circles with different ring spacing and/or different types of bar codes, among other configurations. In some examples, in addition to, or in place of, using markers 212, the contours of known objects, e.g., the side of the access port 12, are captured and identified by using optical imaging devices and the tracking system.

Still referring to FIG. 2B, a guide clamp 218 (or more generally a guide) for holding the access port 12 may be provided. The guide clamp 218 may allow the access port 12 to be held at a fixed position and orientation while freeing up the surgeon's hands. An articulated arm 219 may be provided to hold the guide clamp 218. The articulated arm 219 may have up to six degrees of freedom to position the guide clamp 218. The articulated arm 219 may be lockable to fix its position and orientation, once a desired position is achieved. The articulated arm 219 may be attached or attachable to a point based on the patient head holder 217, or another suitable point, e.g., on another patient support, such as on the surgical bed, to ensure that when locked in place, the guide clamp 218 does not move relative to the patient's head.

Still referring to FIG. 2B, in a surgical operating room (or theatre), setup of a navigation system may be relatively complicated; there may be many pieces of equipment associated with the surgical procedure, as well as elements of the navigation system 205. Further, setup time typically increases as more equipment is added. To assist in addressing this, the navigation system 205 may include two additional wide-field cameras to enable video overlay information. Video overlay information can then be inserted into displayed images, such as images displayed on one or more of the displays 206, 211. The overlay information may illustrate the physical space where accuracy of the 3D tracking system (which is typically part of the navigation system) is greater, may illustrate the available range of motion of the positioning system 208 and/or the imaging system 500, and/or may help to guide head and/or patient positioning.

Still referring to FIG. 2B, the navigation system 205 may provide tools to the neurosurgeon that may help to provide more relevant information to the surgeon, and may assist in improving performance and accuracy of port-based neurosurgical operations. Although described in the present disclosure in the context of port-based neurosurgery, e.g., for removal of brain tumors and/or for treatment of intracranial hemorrhages (ICH), the navigation system 205 may also be suitable for one or more of: brain biopsy, functional/deep-brain stimulation, catheter/shunt placement (in the brain or elsewhere), open craniotomies, and/or endonasal/skull-based/ear-nose-throat (ENT) procedures, among others. The same navigation system 205 may be used for carrying out any or all of these procedures, with or without modification as appropriate.

Still referring to FIG. 2B, for example, although the present disclosure may discuss the navigation system 205 in the context of neurosurgery, the same navigation system 205 may be used to carry out a diagnostic procedure, such as brain biopsy. A brain biopsy may involve the insertion of a thin needle into a patient's brain for purposes of removing a sample of brain tissue. The brain tissue may be subsequently assessed by a pathologist to determine if it is cancerous, for example. Brain biopsy procedures are conducted with or without a stereotactic frame. Both types of procedures are performed using image-guidance. Frameless biopsies, in particular, are conducted using the navigation system 205.

Still referring to FIG. 2B, in some examples, the tracking camera 213 may be part of any suitable tracking system. In some examples, the tracking camera 213, and any associated tracking system that uses the tracking camera 213, are replaced with any suitable tracking system which may or may not use camera-based tracking techniques. For example, a tracking system that does not use the tracking camera 213, such as a radiofrequency tracking system, is used with the navigation system 205.

Figure 3:
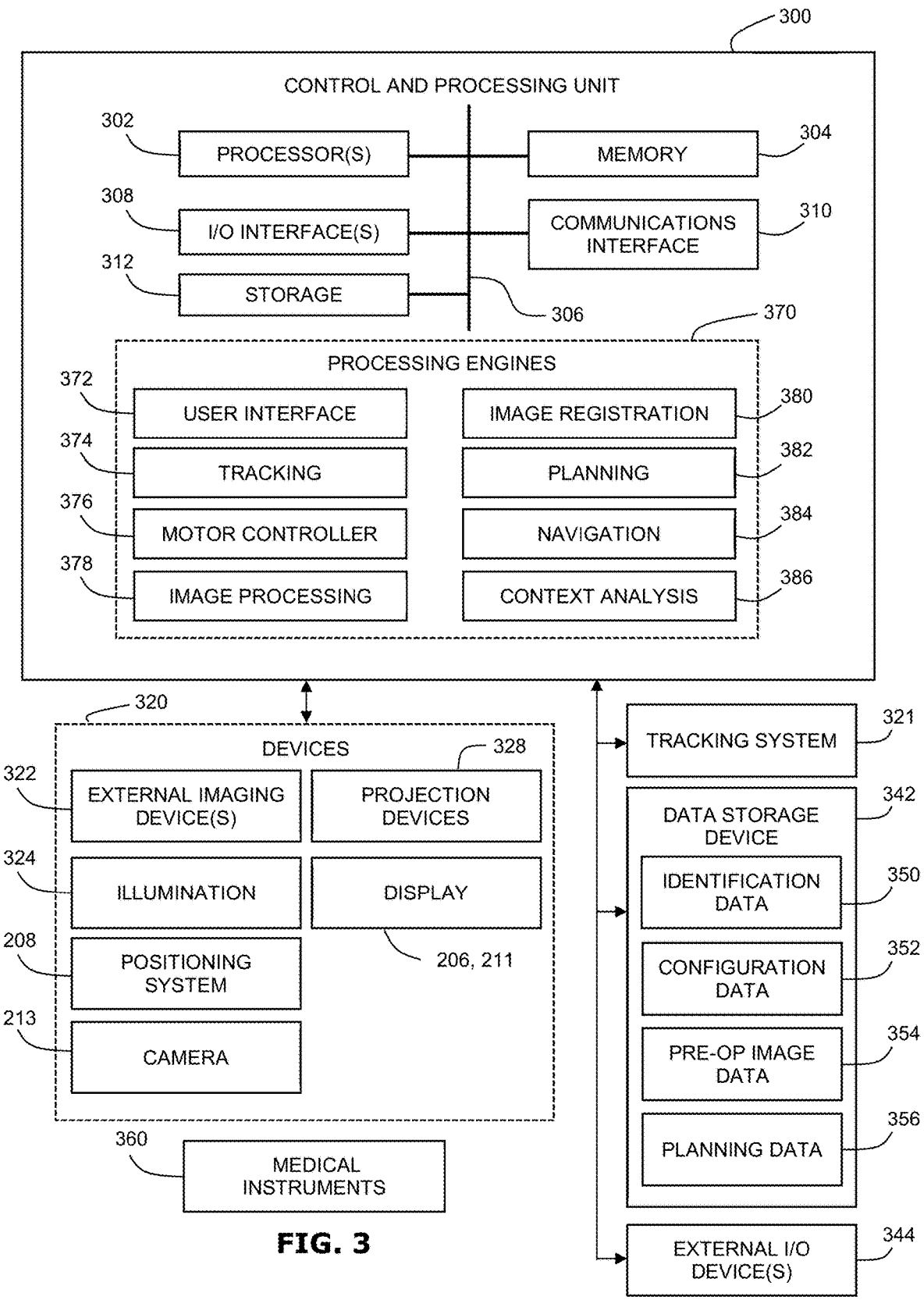
FIG. 3 is a block diagram illustrating an example control and processing system that may be used in the example navigation systems of FIGS. 2A and 2B.

Referring to FIG. 3, this block diagram illustrates a control and processing system 300 usable in the medical navigation system 205, as shown in FIG. 2B, e.g., as part of the equipment tower 207. In one example, the control and processing system 300 comprises one or more processors 302, a memory 304, a system bus 306, one or more input/output interfaces 308, a communications interface 310, and storage device 312. The control and processing system 300 is interfaced with other external devices, such as a tracking system 321, a data storage 342, and external user input and output devices 344, which comprise, for example, one or more of a display, a keyboard, a mouse, sensors attached to medical equipment, a foot pedal, a microphone, and a speaker. Data storage 342 comprises any suitable data storage device, such as a local or remote computing device, e.g. a computer, hard drive, digital media device, or server, having a database stored thereon. The data storage device 342 stores identification data 350 for identifying one or more medical instruments 360 and configuration data 352 that associates customized configuration parameters with one or more medical instruments 360. The data storage device 342 also stores preoperative image data 354 and/or medical procedure planning data 356. Although the data storage device 342 is shown as a single device, in other embodiments, the data storage device 342 comprises a plurality of storage devices.

Still referring to FIG. 3, the medical instruments 360 are identifiable by the control and processing unit 300. The medical instruments 360 are coupled with, and controlled by, the control and processing unit 300, or the medical instruments 360 are operated, or otherwise employed, independent of the control and processing unit 300. The tracking system 321 may be employed to track one or more medical instruments 360 and spatially register the one or more tracked medical instruments to an intraoperative reference frame. For example, the medical instruments 360 may include tracking markers such as tracking spheres that may be recognizable by the tracking camera 213. In one example, the tracking camera 213 may be an infrared (IR) tracking camera. In another example, a sheath placed over a medical instrument 360 may be connected to and controlled by the control and processing unit 300. The control and processing unit 300 may also interface with a number of configurable devices, and may intraoperatively reconfigure one or more of such devices based on configuration parameters obtained from configuration data 352. Examples of devices 320, as shown, comprise one or more external imaging devices 322, one or more illumination devices 324, the positioning system 208, the tracking camera 213, one or more projection devices 328, and one or more displays 206, 211.

Still referring to FIG. 3, exemplary aspects of the disclosure can be implemented via the processor(s) 302 and/or memory 304. For example, the functionalities described herein can be partially implemented via hardware logic in the processor 302 and partially using the instructions stored in the memory 304, as one or more processing modules or engines 370. Example processing modules include, but are not limited to, a user interface engine 372, a tracking module 374, a motor controller 376, an image processing engine 378, an image registration engine 380, a procedure planning engine 382, a navigation engine 384, and a context analysis module 386. While the example processing modules are shown separately, in some examples, the processing modules 370 are stored in the memory 304; and the processing modules 370 are collectively referred to as processing modules 370. In some examples, two or more modules 370 are used together to perform a function. Although depicted as separate modules 370, the modules 370 may comprise a unified set of computer-readable instructions, e.g., stored in the memory 304, rather than distinct sets of instructions. The system is not intended to be limited to the components shown. One or more components of the control and processing system 300 may be provided as an external component or device. In one example, the navigation module 384 may be provided as an external navigation system that is integrated with the control and processing system 300.

Still referring to FIG. 3, some embodiments are implemented by using the processor 302 without additional instructions stored in memory 304. Some embodiments are implemented using the instructions stored in memory 304 for execution by one or more general purpose microprocessors. Thus, the embodiments of the present disclosure are not limited to a specific configuration of hardware and/or software. In some examples, the navigation system 205, comprising the control and processing unit 300, may provide tools to the surgeon that may help to improve the performance of the medical procedure and/or post-operative outcomes. In addition to removal of brain tumours and intracranial hemorrhages (ICH), the navigation system 205 can also be applied to a brain biopsy, a functional/deep-brain stimulation, a catheter/shunt placement procedure, open craniotomies, endonasal/skull-based/ENT, spine procedures, and other parts of the body, such as breast biopsies, liver biopsies, etc. While several examples have been provided, examples of the present disclosure may be applied to any suitable medical procedure.

Figure 4A:
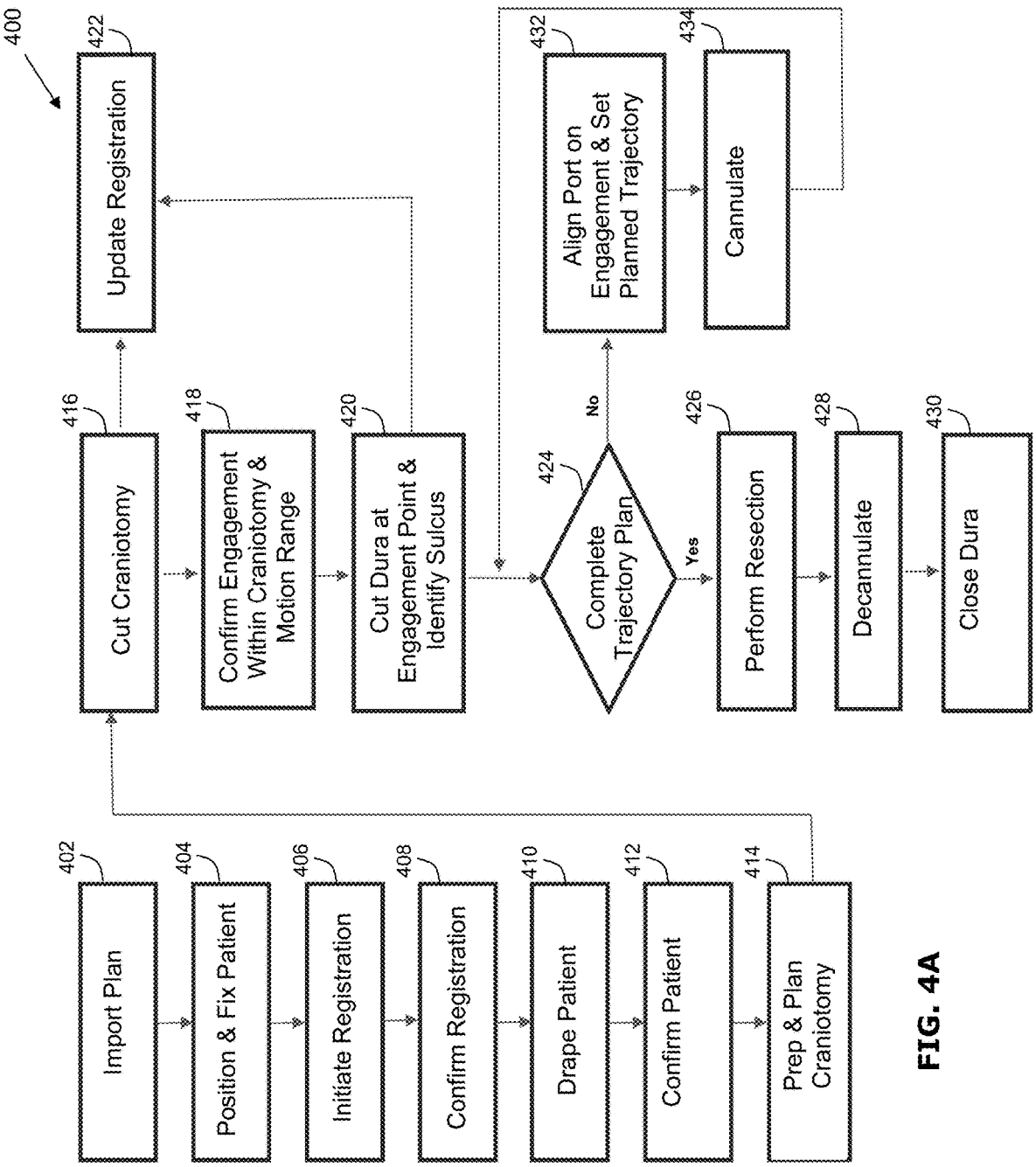
FIG. 4A is a flow chart illustrating an example method involved in a surgical procedure that may be implemented using the example navigation systems of FIGS. 2A and 2B.

Referring to FIG. 4A, this flow chart illustrates an example method 400 of performing a port-based surgical procedure using a navigation system, such as the medical navigation system 205, as shown in FIGS. 2A and 2B. At a first block 402, the port-based surgical plan is imported. Once the plan has been imported into the navigation system at the block 402, the patient is affixed into position using a body holding mechanism. The head position is also confirmed with the patient plan in the navigation system (block 404), which in one example may be implemented by the computer or controller forming part of the equipment tower 207. Next, registration of the patient is initiated (block 406).

The phrase "registration" or "image registration" refers to the process of transforming different sets of data into one coordinate system. Data may include multiple photographs, data from different sensors, times, depths, or viewpoints. The process of "registration" is used in the present application for medical imaging in which images from different imaging modalities are co-registered. Registration is used in order to be able to compare or integrate the data obtained from these different modalities.

Still referring to FIG. 4A, numerous registration techniques are available and one or more of such registration techniques may be applied to the present example. Non-limiting examples include intensity-based methods that compare intensity patterns in images via correlation metrics, while feature-based methods find correspondence between image features such as points, lines, and contours. Image registration methods may also be classified according to the transformation models they use to relate the target image space to the reference image space. Another classification can be made between single-modality and multi-modality methods. Single-modality methods typically register images in the same modality acquired by the same scanner or sensor type, for example, a series of magnetic resonance (MR) images may be co-registered, while multi-modality registration methods are used to register images acquired by different scanner or sensor types, for example, in magnetic resonance imaging (MRI) and positron emission tomography (PET). In the present disclosure, multi-modality registration methods may be used in medical imaging of the head and/or brain as images of a subject are frequently obtained from different scanners. Examples include registration of brain computerized tomography (CT)/MRI images or PET/CT images for tumor localization, registration of contrast-enhanced CT images against non-contrast-enhanced CT images, and registration of ultrasound and CT.

Figure 4B:
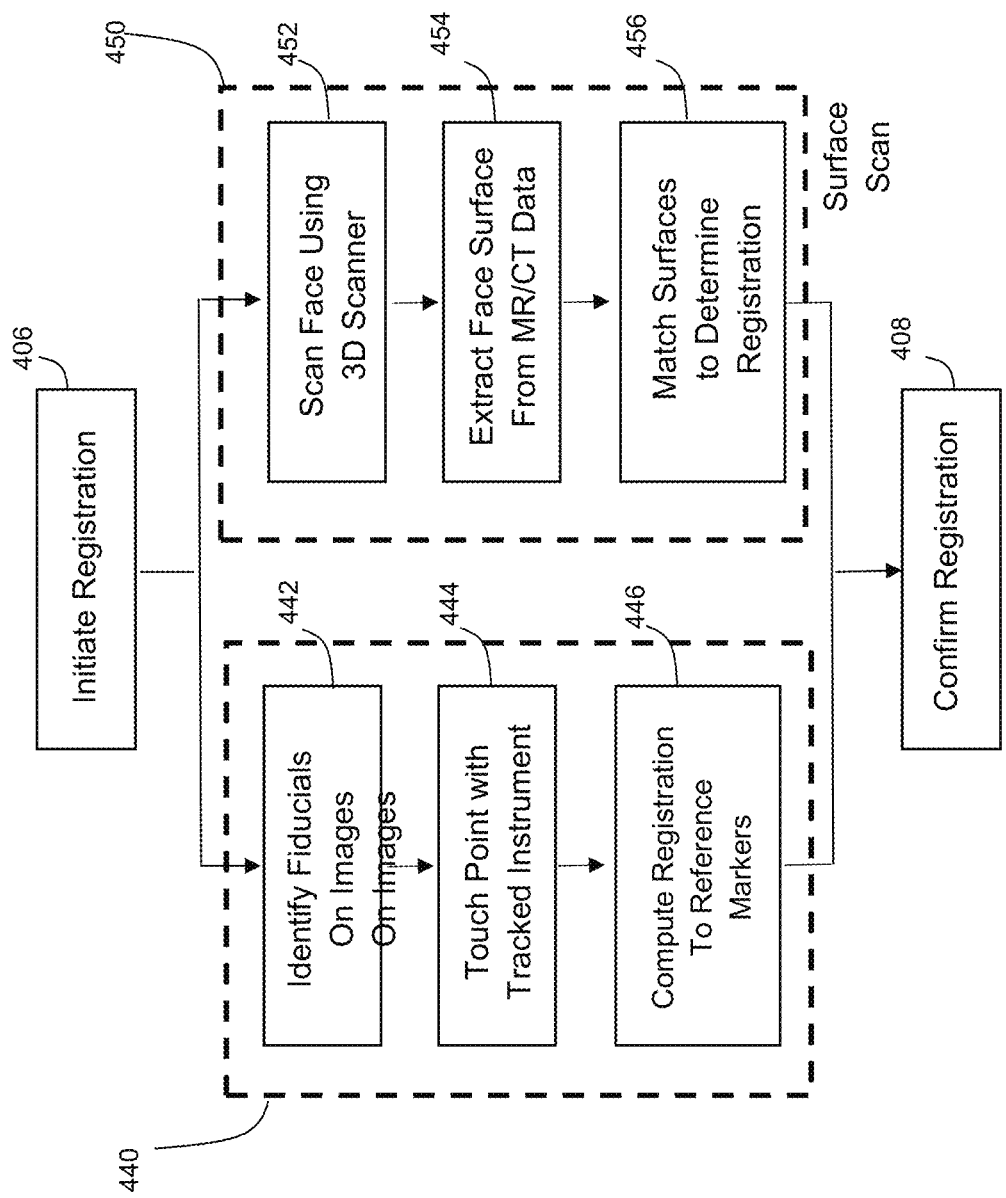
FIG. 4B is a flow chart illustrating an example method of registering a patient for a surgical procedure as outlined in FIG. 4A.

Referring to FIG. 4B, this flow chart illustrates an example method involved in registration block 406, as shown in FIG. 4A, in greater detail. If the use of fiducial touch points 440 is contemplated, the method involves first identifying fiducials on images (block 442), then touching the touch points with a tracked instrument (block 444). Next, the navigation system computes the registration to reference markers (block 446). Alternately, registration can also be completed by conducting a surface scan procedure (block 450). The block 450 is presented to show an alternative approach, but may not typically be used when using a fiducial pointer. First, the face is scanned using a 3D scanner (block 452). Next, the face surface is extracted from MR/CT data (block 454). Finally, surfaces are matched to determine registration data points (block 456). Upon completion of either the fiducial touch points 440 or surface scan 450 procedures, the data extracted is computed and used to confirm registration at block 408, as shown in FIG. 4A.

Referring back to FIG. 4A, once registration is confirmed (block 408), the patient is draped (block 410). Typically, draping involves covering the patient and surrounding areas with a sterile barrier to create and maintain a sterile field during the surgical procedure. The purpose of draping is to eliminate the passage of microorganisms, e.g., bacteria, between non-sterile and sterile areas. At this point, conventional navigation systems require that the non-sterile patient reference is replaced with a sterile patient reference of identical geometry location and orientation. Upon completion of draping (block 410), the patient engagement points are confirmed (block 412) and then the craniotomy is prepared and planned (block 414). Upon completion of the preparation and planning of the craniotomy (block 414), the craniotomy is cut and a bone flap is temporarily removed from the skull to access the brain (block 416). Registration data is updated with the navigation system at this point (block 422). Next, the engagement within craniotomy and the motion range are confirmed (block 418). Next, the procedure advances to cutting the dura at the engagement points and identifying the sulcus (block 420).

Still referring back to FIG. 4A, thereafter, the cannulation process is initiated (block 424). Cannulation involves inserting a port into the brain, typically along a sulci path as identified at 420, along a trajectory plan. Cannulation is typically an iterative process that involves repeating the steps of aligning the port on engagement and setting the planned trajectory (block 432) and then cannulating to the target depth (block 434) until the complete trajectory plan is executed (block 424). Once cannulation is complete, the surgeon then performs resection (block 426) to remove part of the brain and/or tumor of interest. The surgeon then decannulates (block 428) by removing the port and any tracking instruments from the brain. Finally, the surgeon closes the dura and completes the craniotomy (block 430). Some aspects of FIG. 4A are specific to port-based surgery, such as portions of blocks 428, 420, and 434, but the appropriate portions of these blocks may be skipped or suitably modified when performing non-port based surgery.

Referring back to FIGS. 4A and 4B, when performing a surgical procedure using a medical navigation system 205, the medical navigation system 205 may acquire and maintain a reference of the location of the tools in use as well as the patient in three dimensional (3D) space. During a navigated neurosurgery, a tracked reference frame exists that is fixed, e.g., relative to the patient's skull. During the registration phase of a navigated neurosurgery, e.g., the step 406 shown in FIGS. 4A and 4B, a transformation is calculated that maps the frame of reference of preoperative MRI or CT imagery to the physical space of the surgery, specifically the patient's head. This may be accomplished by the navigation system 205 tracking locations of fiducial markers fixed to the patient's head, relative to the static patient reference frame. The patient reference frame is typically rigidly attached to the head fixation device, such as a Mayfield® clamp. Registration is typically performed before the sterile field has been established, e.g., via the step 410.

Figure 5:
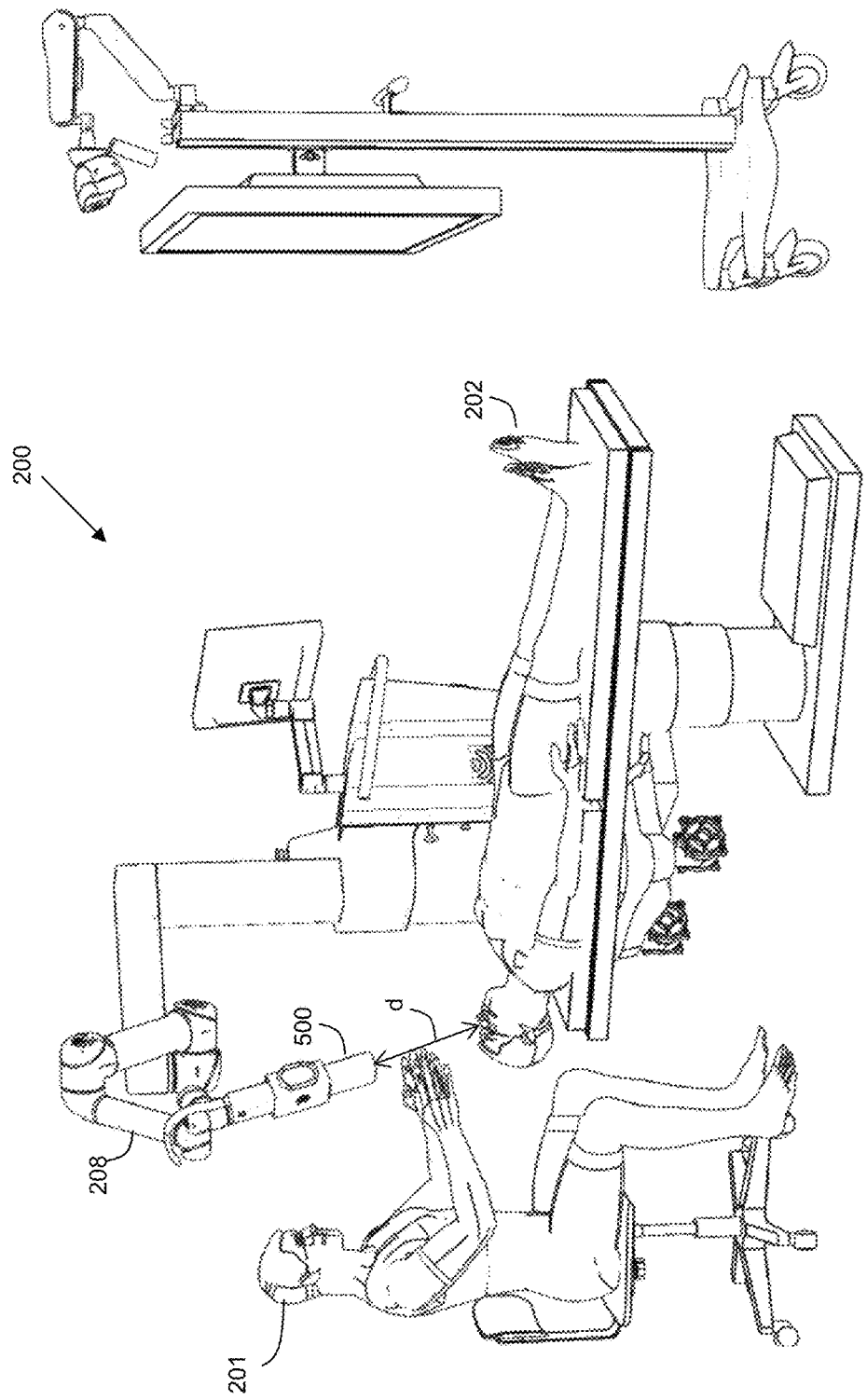
FIG. 5 is a diagram illustrating the use of an example optical imaging system during a medical procedure.

Referring to FIG. 5, this diagram illustrates use of an example imaging system 500, described further below, in a medical procedure. Although the imaging system 500 is shown as being used in the context of a navigation system environment 200, e.g., using a navigation system as described above, the imaging system 500 may also be used outside of a navigation system environment, e.g., without any navigation support. An operator, typically a surgeon 201, may use the imaging system 500 to observe the surgical site, e.g., to look down an access port 12. The imaging system 500 may be attached to a positioning system 208, e.g., a controllable and adjustable robotic arm. The position and orientation of the positioning system 208, imaging system 500 and/or access port may be tracked using a tracking system, such as described for the navigation system 205. The distance d between the imaging system 500 (more specifically, the aperture of the imaging system 500) and the viewing target, e.g., the surface of the surgical site, are referred as the "working distance." The imaging system 500 is configured for use in a predefined range of working distance, e.g., in the range of about 15 cm to about 75 cm. If the imaging system 500 is mounted on the positioning system 208, the actual available range of working distance may be dependent on both the working distance of the imaging system 500 as well as the workspace and kinematics of the positioning system 208.

Figure 6:
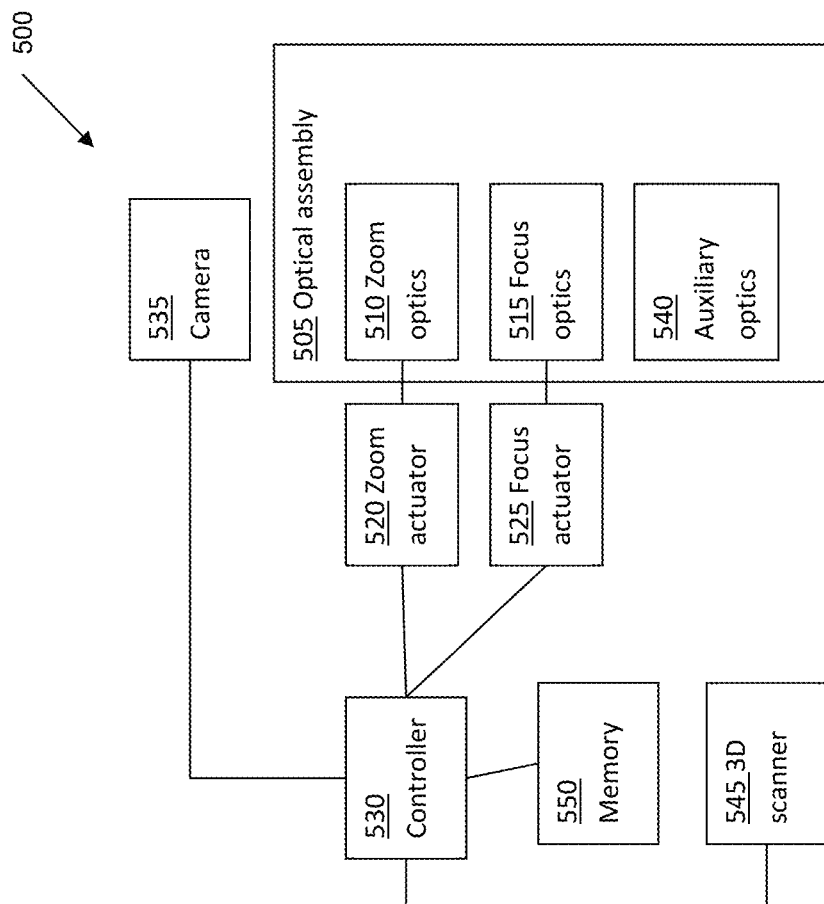
FIG. 6 is a block diagram illustrating an example optical imaging system.

Referring to FIG. 6, this block diagram illustrates components of an example imaging system 500. The imaging system 500 comprises an optical assembly 505 (also referred to as an optical train). The optical assembly 505 comprises optics, e.g., lenses, optical fibers, etc., for focusing and zooming on the viewing target. The optical assembly 505 may include zoom optics 510 (which may include one or more zoom lenses) and focus optics 515 (which may include one or more focus lenses). Each of the zoom optics 510 and focus optics 515 are independently moveable within the optical assembly, in order to adjust the zoom and focus, respectively. Where the zoom optics 510 and/or the focus optics 515 include more than one lens, each individual lens may be independently moveable. The optical assembly 505 may include an aperture (not shown), which may be adjustable.

Still referring to FIG. 6, the imaging system 500 comprises a zoom actuator 520 and a focus actuator 525 for positioning the zoom optics 510 and the focus optics 515, respectively. The zoom actuator 520 and/or the focus actuator 525 comprises an electric motor, or other types of actuators including, for example, pneumatic actuators, hydraulic actuators, shape-changing materials, e.g., piezoelectric materials or other smart materials, or engines, among other possibilities. Although the term "motorized" is used in the present disclosure, understood is that the use of this term does not limit the present disclosure to use of motors necessarily, but is intended to cover all suitable actuators, including motors. Although the zoom actuator 520 and the focus actuator 525 are shown outside of the optical assembly 505, in some examples the zoom actuator 520 and the focus actuator 525 may be part of or integrated with the optical assembly 505. The zoom actuator 520 and the focus actuator 525 may operate independently, to control positioning of the zoom optics 510 and the focus optics 515, respectively. The lens(es) of the zoom optics 510 and/or the focus optics 515 may be each mounted on a linear stage, e.g., a motion system that restricts an object to move in a single axis, which may include a linear guide and an actuator; or a conveyer system such as a conveyor belt mechanism, that is moved by the zoom actuator 520 and/or the focus actuator 525, respectively, to control positioning of the zoom optics 510 and/or the focus optics 515. In some examples, the zoom optics 510 may be mounted on a linear stage that is driven, via a belt drive, by the zoom actuator 520, while the focus optics 515 is geared to the focus actuator 525. The independent operation of the zoom actuator 520 and the focus actuator 525 may enable the zoom and focus to be adjusted independently. Thus, when an image is in focus, the zoom may be adjusted without requiring further adjustments to the focus optics 515 to produce a focused image.

Still referring to FIG. 6, operation of the zoom actuator 520 and the focus actuator 525 is controlled by a controller 530, e.g., a microprocessor, of the imaging system 500. The controller 530 receives control input, e.g., from an external system, such as an external processor or an input device. The control input indicates a desired zoom and/or focus; and the controller 530 may, in response, cause the zoom actuator 520 and/or focus actuator 525 to move the zoom optics 510 and/or the focus optics 515, accordingly, to achieve the desired zoom and/or focus. In some examples, the zoom optics 510 and/or the focus optics 515 may be moved or actuated without the use of the zoom actuator 520 and/or the focus actuator 525. For example, the focus optics 515 uses electrically-tunable lenses or other deformable material controlled directly by the controller 530.

Still referring to FIG. 6, by providing the controller 530, the zoom actuator 520 and the focus actuator 525 all as part of the imaging system 500, the imaging system 500 may enable an operator, e.g., a surgeon, to control zoom and/or focus during a medical procedure without having to manually adjust the zoom and/or focus optics 510, 515. For example, the operator may provide control input to the controller 530 verbally, e.g., via a voice recognition input system, by instructing an assistant to enter control input into an external input device, e.g., into a user interface provided by a workstation, using a foot pedal, or by other such user interface apparatus. In some examples, the controller 530 may carry out preset instructions to maintain the zoom and/or focus at preset values, e.g., to perform autofocusing, without requiring further control input during the medical procedure.

Still referring to FIG. 6, an external processor, e.g., a processor of a workstation or the navigation system, in communication with the controller 530 may be used to provide control input to the controller 530. For example, the external processor may provide a graphical user interface via which the operator or an assistant may input instructions to control zoom and/or focus of the imaging system 500. The controller 530 may alternatively or additionally be in communication with an external input system, e.g., a voice recognition input system or a foot pedal. The optical assembly 505 may also include one or more auxiliary optics 540, e.g., an adjustable aperture, which may be static or dynamic. Where the auxiliary optics 540 is dynamic, the auxiliary optics 540 may be moved using an auxiliary actuator (not shown) which may be controlled by the controller 530.

Still referring to FIG. 6, the imaging system 500 may also include a camera 535, e.g., a high-definition (HD) camera, that captures image data from the optical assembly. Operation of the camera may be controlled by the controller 530. The camera 535 may also output data to an external system, e.g., an external workstation or external output device, to view the captured image data. In some examples, the camera 535 may output data to the controller 530, which in turn transmits the data to an external system for viewing. By providing image data to an external system for viewing, the captured images may be viewed on a larger display and may be displayed together with other information relevant to the medical procedure, e.g., a wide-field view of the surgical site, navigation markers, 3D images, etc. Providing the camera 535 with the imaging system 500 may help to improve the consistency of image quality among different medical centers. Image data captured by the camera 535 may be displayed on a display together with a wide-field view of the surgical site, for example in a multiple-view user interface. The portion of the surgical site that is captured by the camera 535 may be visually indicated in the wide-field view of the surgical site.

Still referring to FIG. 6, the imaging system 500 comprises a three-dimensional (3D) scanner 545 or 3D camera for obtaining 3D information of the viewing target. The 3D information from the 3D scanner 545 may also be captured by the camera 535, or may be captured by the 3D scanner 545 itself. Operation of the 3D scanner 545 may be controlled by the controller 530, and the 3D scanner 545 may transmit data to the controller 530. In some examples, the 3D scanner 545 may itself transmit data to an external system, e.g., an external workstation. The 3D information from the 3D scanner 545 may be used to generate a 3D image of the viewing target, e.g., a 3D image of a target tumor that is to be resected. The 3D information may also be useful in an augmented reality (AR) display provided by an external system. For example, an AR display, e.g., provided via AR glasses, may, using information from a navigation system to register 3D information with optical images, overlay a 3D image of a target specimen on a real-time optical image, e.g., an optical image captured by the camera 535.

Still referring to FIG. 6, the controller 530 may be coupled to a memory 550. The memory 550 may be internal or external of the imaging system 500. Data received by the controller 530, e.g., image data from the camera 535 and/or 3D data from the 3D scanner, may be stored in the memory 550. The memory 550 may also contain instructions to enable the controller to operate the zoom actuator 520 and the focus actuator 525. For example, the memory 550 may store instructions to enable the controller to perform autofocusing, as discussed further below. The imaging system 500 may communicate with an external system, e.g., a navigation system or a workstation, via wired or wireless communication. In some examples, the imaging system 500 may include a wireless transceiver (not shown) to enable wireless communication. In some examples, the imaging system 500 may include a power source, e.g., a battery, or a connector to a power source, e.g., an AC adaptor. In some examples, the imaging system 500 may receive power via a connection to an external system, e.g., an external workstation or processor.

Still referring to FIG. 6, in some examples, the imaging system 500 may include a light source (not shown). In some examples, the light source may not itself generate light but rather direct light from another light generating component. For example, the light source may be an output of a fiber optics cable connected to another light generating component, which may be part of the imaging system 500 or external to the imaging system 500. The light source may be mounted near the aperture of the optical assembly, to direct light to the viewing target. Providing the light source with the imaging system 500 may help to improve the consistency of image quality among different medical centers. In some examples, the power or output of the light source may be controlled by the imaging system 500, e.g., by the controller 530, or may be controlled by a system external to the imaging system 500, e.g., by an external workstation or processor, such as a processor of a navigation system.

Still referring to FIG. 6, in some examples, the optical assembly 505, zoom actuator 520, focus actuator 525 and camera 535 may all be housed within a single housing (not shown) of the imaging system. In some examples, the controller 530, memory 550, 3D scanner 545, wireless transceiver, power source and/or light source may also be housed within the housing. In some examples, the imaging system 500 may also provide mechanisms to enable manual adjusting of the zoom and/or focus optics 510, 515, similarly to conventional systems. Such manual adjusting may be enabled in addition to motorized adjusting of zoom and focus. In some examples, such manual adjusting may be enabled in response to user selection of a "manual mode" on a user interface.

Still referring to FIG. 6, the imaging system 500 may be mountable on a moveable support structure, such as the positioning system, e.g., robotic arm, of a navigation system, a manually operated support arm, a ceiling mounted support, a moveable frame, or other such support structure. The imaging system 500 may be removably mounted on the moveable support structure. In some examples, the imaging system 500 may include a support connector, e.g., a mechanical coupling, to enable the imaging system 500 to be quickly and easily mounted or dismounted from the support structure. The support connector on the imaging system 500 may be configured to be suitable for connecting with a typical complementary connector on the support structure, e.g., as designed for typical end effectors. In some examples, the imaging system 500 may be mounted to the support structure together with other end effectors, or may be mounted to the support structure via another end effector. When mounted, the imaging system 500 may be at a known fixed position and orientation relative to the support structure, e.g., by calibrating the position and orientation of the imaging system 500 after mounting. In this way, by determining the position and orientation of the support structure, e.g., using a navigation system or by tracking the movement of the support structure from a known starting point, the position and orientation of the imaging system 500 may also be determined. In some examples, the imaging system 500 may include a manual release button that, when actuated, enables the imaging system 500 to be manually positioned, e.g., without software control by the support structure.

Still referring to FIG. 6, in some examples, where the imaging system 500 is intended to be used in a navigation system environment, the imaging system 500 may include an array of trackable markers, which may be mounted on a frame on the imaging system 500, to enable the navigation system to track the position and orientation of the imaging system 500. Alternatively or additionally, the moveable support structure, e.g., a positioning system of the navigation system, on which the imaging system 500 is mounted may be tracked by the navigation system and the position and orientation of the imaging system 500 may be determined using the known position and orientation of the imaging system 500 relative to the moveable support structure. The trackable markers may include passive reflective tracking spheres, active infrared (IR) markers, active light emitting diodes (LEDs), a graphical pattern, or a combination thereof. There may be at least three trackable markers provided on a frame to enable tracking of position and orientation. In some examples, there may be four passive reflective tracking spheres coupled to the frame. While some specific examples of the type and number of trackable markers have been given, any suitable trackable marker and configuration may be used, as appropriate. Determination of the position and orientation of the imaging system 500 relative to the viewing target may be performed by a processor external to the imaging system 500, e.g., a processor of the navigation system. Information about the position and orientation of the imaging system 500 may be used, together with a robotic positioning system, to maintain alignment of the imaging system 500 with the viewing target, e.g., to view down an access port during port-based surgery, throughout the medical procedure.

Still referring to FIG. 6, for example, the navigation system may track the position and orientation of the positioning system and/or the imaging system 500 either collectively or independently. Using this information as well as tracking of the access port, the navigation system may determine the desired joint positions for the positioning system so as to maneuver the imaging system 500 to the appropriate position and orientation to maintain alignment with the viewing target, e.g., the longitudinal axes of the imaging system 500 and the access port being aligned. This alignment may be maintained throughout the medical procedure automatically, without requiring explicit control input. In some examples, the operator may be able to manually move the positioning system and/or the imaging system 500, e.g., after actuation of a manual release button. During such manual movement, the navigation system may continue to track the position and orientation of the positioning system and/or the imaging system 500. After completion of manual movement, the navigation system may, e.g., in response to user input, such as using a foot pedal, indicating that manual movement is complete, reposition and reorient the positioning system and the imaging system 500 to regain alignment with the access port.

Still referring to FIG. 6, the controller 530 may use information about the position and orientation of the imaging system 500 to perform autofocusing. For example, the controller 530 may determine the working distance between the imaging system 500 and the viewing target and thus determine the desired positioning of the focus optics 515, e.g., using appropriate equations to calculate the appropriate positioning of the focus optics 515 to achieve a focused image, and move the focus optics 515, using the focus actuator 525, in order to bring the image into focus. For example, the position of the viewing target may be determined by a navigation system. The working distance may be determined by the controller 530 using information, e.g., received from the navigation system, from the positioning system or other external system, about the position and orientation of the imaging system 500 and/or the positioning system relative to the viewing target. In some examples, the working distance may be determined by the controller 530 using an infrared light (not shown) mounted on near the distal end of the imaging system 500.

Still referring to FIG. 6, in some examples, the controller 530 may perform autofocusing without information about the position and orientation of the imaging system 500. For example, the controller 530 may control the focus actuator 525 to move the focus optics 515 into a range of focus positions and control the camera 535 to capture image data at each focus position. The controller 530 may then perform image processing on the captured images to determine which focus position has the sharpest image and determine this focus position to be the desired position of the focus optics 515. The controller 530 may then control the focus actuator 525 to move the focus optics 515 to the desired position. Any other autofocus routine, such as those suitable for handheld cameras, may be implemented by the controller 530 as appropriate.

Still referring to FIG. 6, in some examples, the viewing target may be dynamically defined by the surgeon, e.g., using a user interface provided by a workstation, by touching the desired target on a touch-sensitive display, by using eye or head tracking to detect a point at which the surgeon's gaze is focused and/or by voice command, and the imaging system 500 may perform autofocusing to dynamically focus the image on the defined viewing target. This may enable the surgeon to focus an image on different points within a field of view, without changing the field of view and without having to manually adjust the focus of the imaging system 500.

Figure 11:
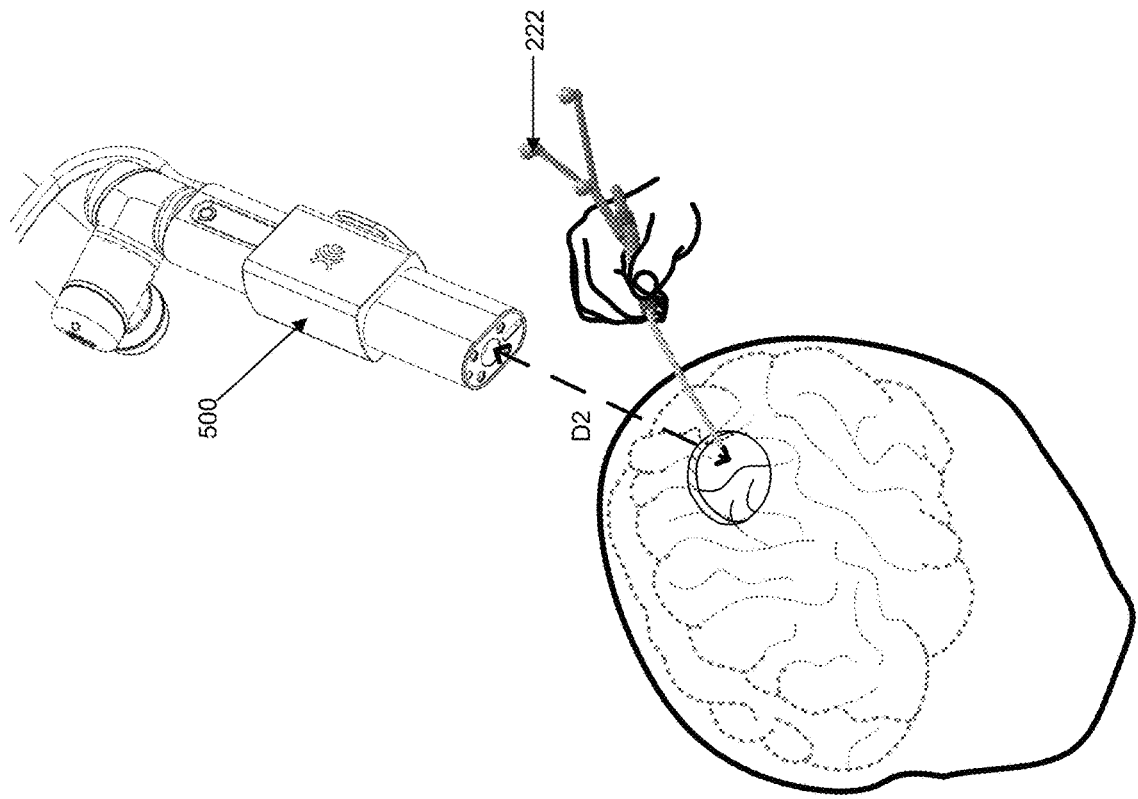
FIG. 11 is a diagram illustrating an example method of autofocusing relative to a medical instrument, using an example optical imaging system.
Figure 11:
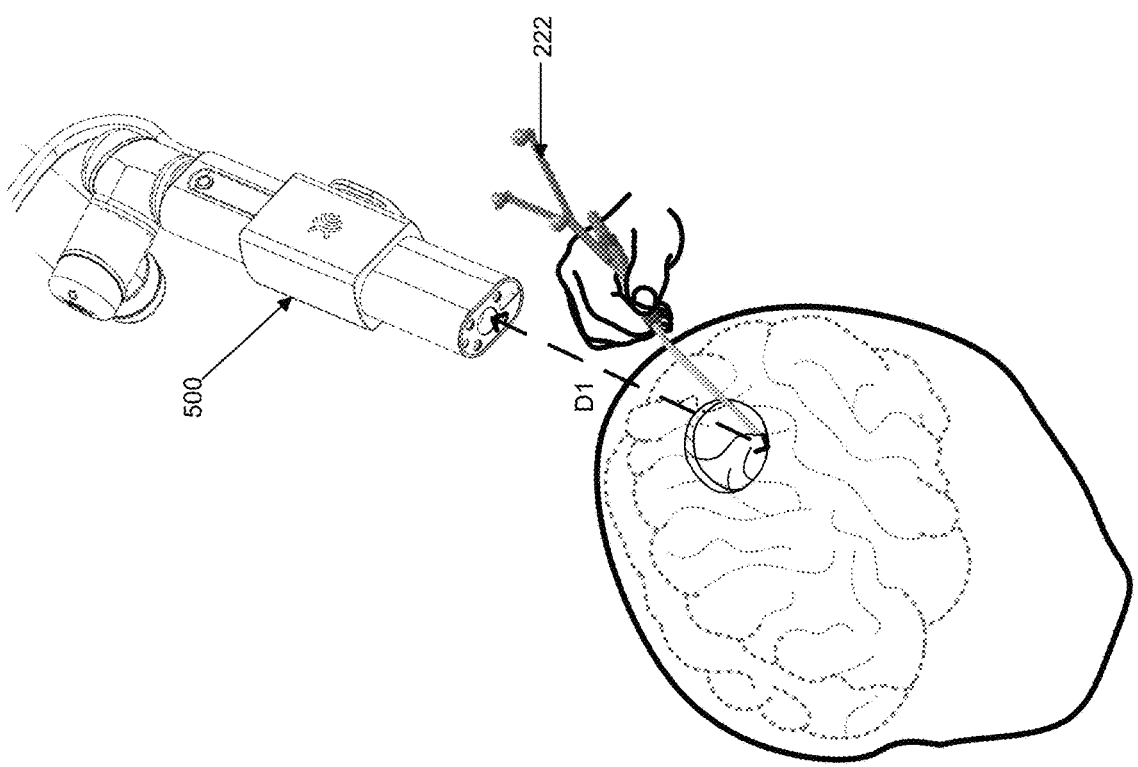

Still referring to FIG. 6 and ahead to FIG. 11, in some examples, the imaging system 500 may be configured to perform autofocusing relative to an instrument using in the medical procedure. For example, the position and orientation of a medical instrument, such as a tracked pointer 222, may be determined and the controller 530 may perform autofocusing to focus the captured image on a point defined relative to the medical instrument. The tracked pointer 222 may have a defined focus point at the distal tip of the pointer 222. As the tracked pointer 222 is moved, the working distance between the optical imaging system 500 and the defined focus point (at the distal tip of the tracked pointer 222) changes (from D1 in the left image to D2 in the right image, for example). The autofocusing may be performed similarly to that described above, however instead of autofocusing on a viewing target in the surgical field, the imaging system 500 may focus on a focus point that is defined relative to the medical instrument. The medical instrument may be used in the surgical field to guide the imaging system 500 to autofocus on different points in the surgical field, as below discussed. This may enable a surgeon to change the focus within a field of view, e.g., focus on a point other than at the center of the field of view, without changing the field of view and without needing to manually adjust the focus of the imaging system 500. Where the field of view includes objects at different depths, the surgeon may use the medical instrument, e.g., a pointer, to indicate to the imaging system 500 the object and/or depth desired for autofocusing.

Still referring to FIG. 6 and ahead to FIG. 11, for example, the controller 530 may receive information about the position and orientation of a medical instrument. This position and orientation information may be received from an external source, e.g., from an external system tracking the medical instrument or from the medical instrument itself, or may be received from another component of the imaging system 500, e.g., an infrared sensor or a machine vision component of the imaging system 500. The controller 530 may determine a focus point relative to the position and orientation of the medical instrument. The focus point may be predefined for a given medical instrument, e.g., the distal tip of a pointer, the distal end of a catheter, the distal end of an access port, the distal end of a soft tissue resector, the distal end of a suction, the target of a laser, or the distal tip of a scalpel, and may be different for different medical instruments. The controller 530 may use this information, together with information about the known position and orientation of the imaging system 500, e.g., determined as discussed above, in order to determine the desired position of the focus optics 515 to achieve an image focused on the focus point defined relative to the medical instrument.

Still referring to FIG. 6 and back to FIG. 2B, in examples where the imaging system 500 is used with a navigation system 205, the position and orientation of a medical instrument, e.g., a tracked pointer 222 or a tracked port 210, may be tracked and determined by the navigation system 205. The controller 530 of the imaging system 500 may automatically autofocus the imaging system 500 to a predetermined point relative to the tracked medical instrument, e.g., autofocus on the tip of the tracked pointer 222 or on the distal end of the access port 210. Autofocusing may be performed relative to other medical instruments and other tools that may be used in the medical procedure. In some examples, the imaging system 500 may be configured to perform autofocusing relative to a medical instrument only when it is determined that the focus point relative to the medical instrument is within the field of view of the imaging system 500. This may avoid an unintentional change of focus when a medical instrument is moved in the vicinity of but outside the field of view of the imaging system 500. In examples where the imaging system 500 is mounted on a moveable support system, e.g., a robotic arm, if the focus point of the medical instrument is outside of the current field of view of the imaging system 500, the moveable support system may position and orient the imaging system 500 to bring the focus point of the medical instrument within the field of view of the imaging system 500, in response to input, e.g., in response to user command via a user interface or voice input, or via activation of a foot pedal.

Still referring to FIG. 6 and back to FIG. 2B, the imaging system 500 may be configured to implement a small time lag before performing autofocus relative to a medical instrument, in order to avoid erroneously changing focus while the focus point of the medical instrument is brought into and out of the field of view. For example, the imaging system 500 may be configured to autofocus on the focus point only after it has been substantially stationary for a predetermined length of time, e.g., 0.5 second to 1 second. In some examples, the imaging system 500 may also be configured to performing zooming with the focus point as the zoom center. For example, while a focus point is in the field of view or after autofocusing on a certain point in the field of view, the user may provide command input, e.g., via a user interface, voice input or activation of a foot pedal, to instruct the imaging system 500 to zoom in on the focus point. The controller 530 may then position the zoom optics 520 accordingly to zoom in on the focus point. Where appropriate, the positioning system (if the imaging system 500 is mounted on a positioning system) may automatically reposition the imaging system 500 as needed to center the zoomed in view on the focus point.

Still referring to FIG. 6 and back to FIG. 2B, in some examples, the imaging system 500 may automatically change between different autofocus modes. For example, if the current field of view does not include any focus point defined by a medical instrument, the controller 530 may perform autofocus based on a preset criteria, e.g., to obtain the sharpest image or to focus on the center of the field of view. When a focus point defined by a medical instrument is brought into the field of view, the controller 530 may automatically switch mode to autofocus on the focus point. In some examples, the imaging system 500 may change between different autofocus modes in response to user input, e.g., in response to user command via a user interface, voice input, or activation of a foot pedal. In various examples of autofocusing, whether or not relative to a medical instrument, the imaging system 500 may be configured to maintain the focus as the zoom is adjusted.

Still referring to FIG. 6 and back to FIG. 2B, in some examples, the imaging system 500 may generate a depth map. This may be performed by capturing images of the same field of view, but with the imaging system 500 focused on points at different depths to simulate 3D depth perception. For example, the imaging system 500 may automatically perform autofocusing through a predefined depth range, e.g., through a depth of about 1 cm, and capturing focused images at different depths, e.g., at increments of 1 mm, through the depth range. The images captured at different depths may be transmitted to an external system, e.g., an image viewing workstation, where they may be aggregated into a set of depth images to form a depth map for the same field of view. The depth map may provide focused views of the field of view, at different depths, and may include contours, color-coding and/or other indicators of different depths. The external system may provide a user interface that allows a user to navigate through the depth map. In some examples, the optical imaging system 500 could be configured with a relatively large depth of field. The 3D scanner 545 may be used to create a depth map of the viewed area, and the depth map may be registered to the image captured by the camera 535. Image processing may be performed, e.g., using the controller 530 or an external processor, to generate a pseudo 3D image, for example by visually encoding, e.g., using color, artificial blurring or other visual symbols, different parts of the captured image according to the depth information from the 3D scanner 545.

Figure 7:
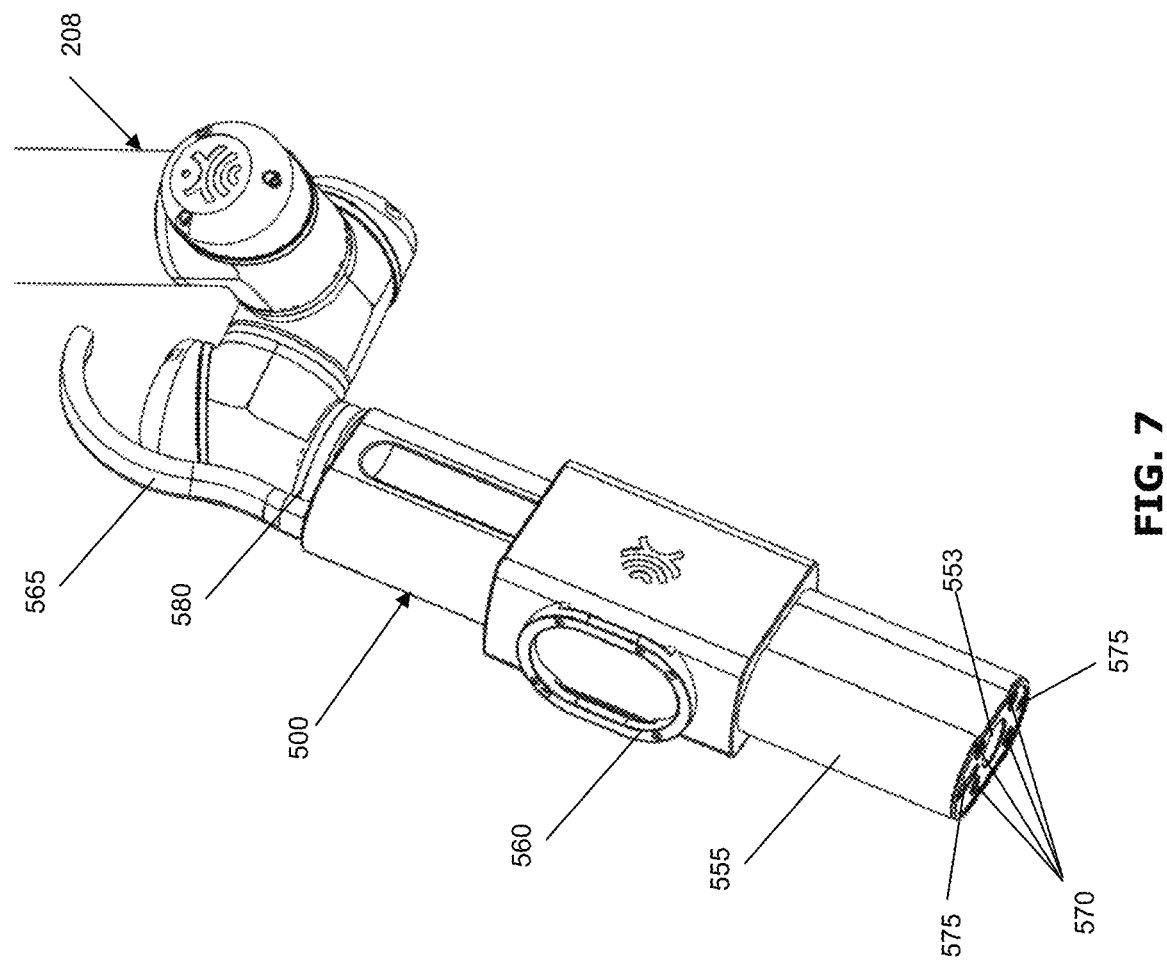
FIGS. 7 and 8 are diagrams illustrating different perspective views of an example optical imaging system.
Figure 8:
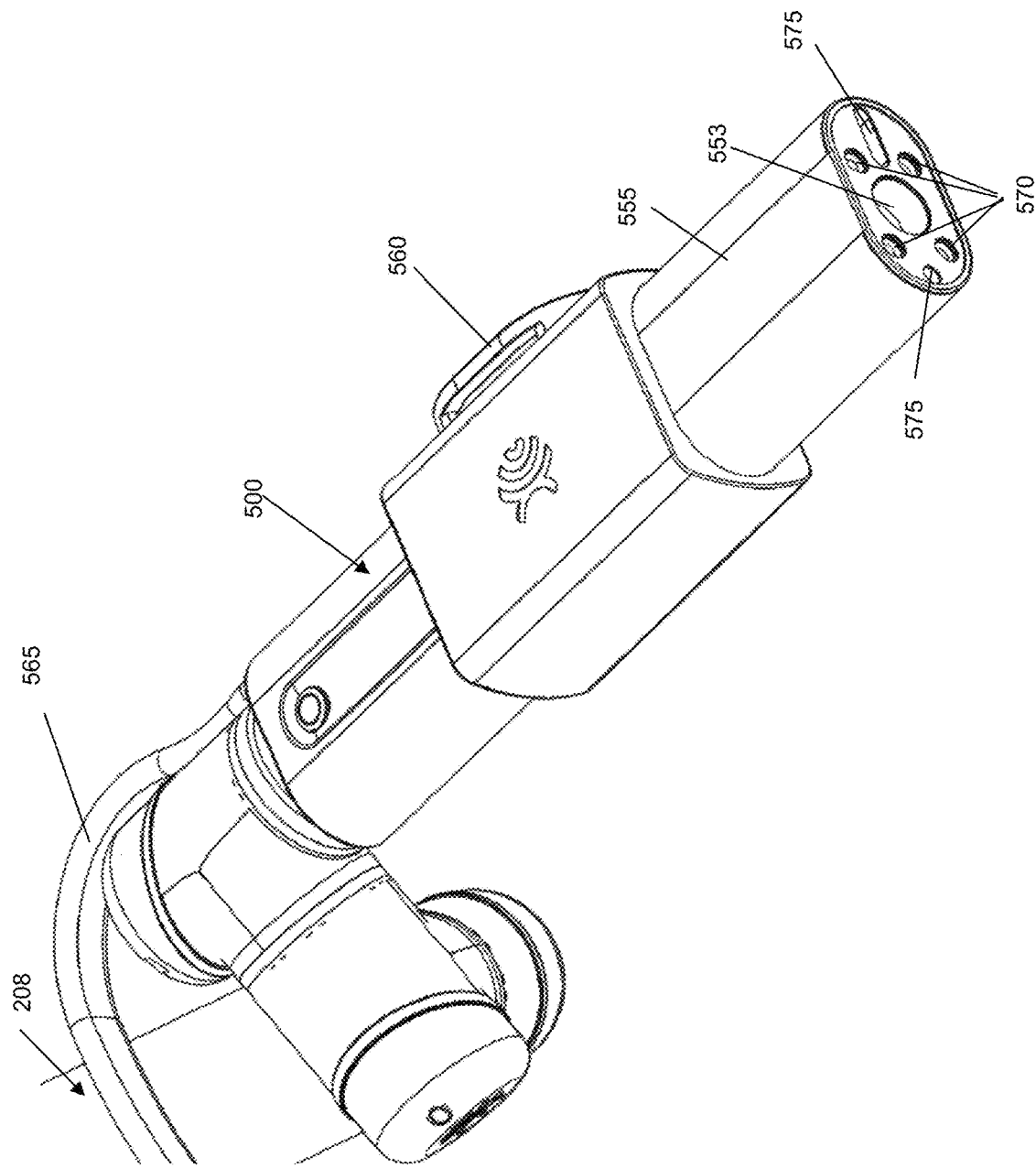

Referring to FIGS. 7 and 8, these diagrams illustrate perspective views of an example embodiment of the imaging system 500. In this example, the imaging system 500 is shown mounted to the positioning system 208, e.g., a robotic arm, of a navigation system. The imaging system 500 is shown with a housing 555 that encloses the zoom and focus optics, the zoom and focus actuators, the camera, the controller and the 3D scanner. The housing is provided with a frame 560 on which trackable markers may be mounted, to enable tracking by the navigation system. The imaging system 500 communicates with the navigation system via a cable 565 (shown cutoff). The distal end of the imaging system 500 is provided with light sources 570. The example shows four broad spectrum LEDs, however more or less light sources may be used, of any suitable type. Although the light sources 570 are shown provided surrounding the aperture 553 of the imaging system 500, in other examples the light source(s) 570 may be located elsewhere on the imaging system 500. The distal end of the imaging system 500 may also include openings 575 for the cameras of the integrated 3D scanner. A support connector 580 for mounting the imaging system 500 to the positioning system 208 is also shown, as well as the frame 560 for mounting trackable markers.

Figure 9:
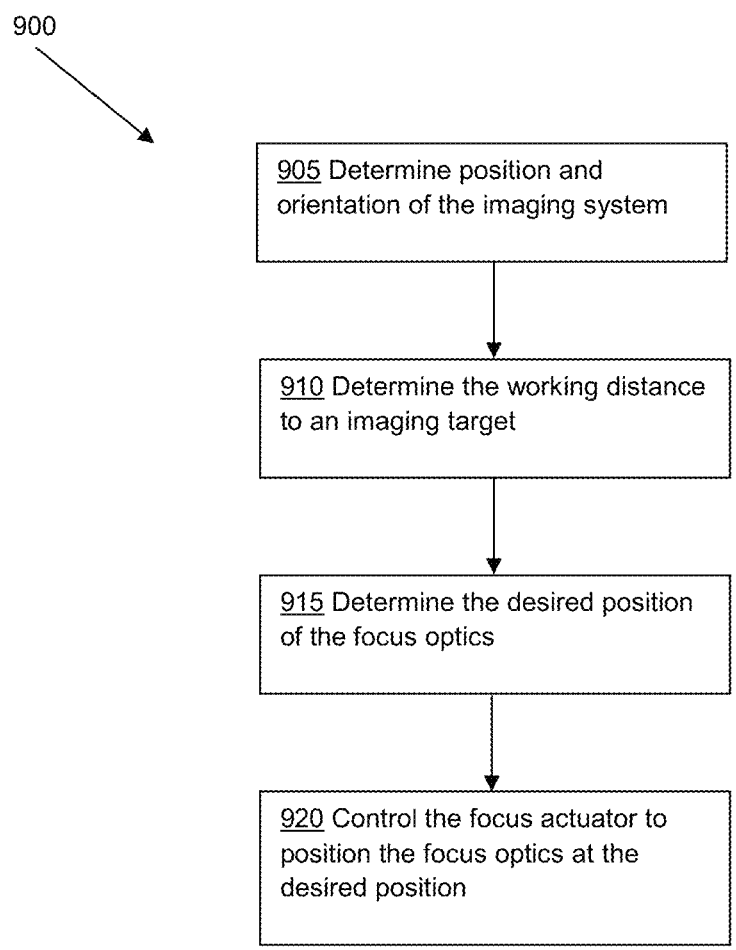
FIG. 9 is a flowchart illustrating an example method of autofocusing using an example optical imaging system.

Referring to FIG. 9, this flowchart illustrates an example method 900 of autofocusing during a medical procedure. The method 900 may be performed using an example optical imaging system, as disclosed herein. At step 905, the position and orientation of the imaging system are determined. This may be done by tracking the imaging system, by performing calibration, or by tracking the positioning system on which the imaging system is mounted, for example. At step 910, the working distance between the imaging system and the imaging target is determined. For example, the position of the imaging target may be determined by a navigation system, and this information may be used together with the position and orientation information of the imaging system to determine the working distance. At step 915, the desired position of the focus optics is determined, in order to achieve a focused image. At step 920, the focus actuator is controlled, e.g., by a controller of the imaging system, to position the focus optics at the desired position. A focused image may then be captured, for example using a camera of the optical imaging system.

Figure 10:
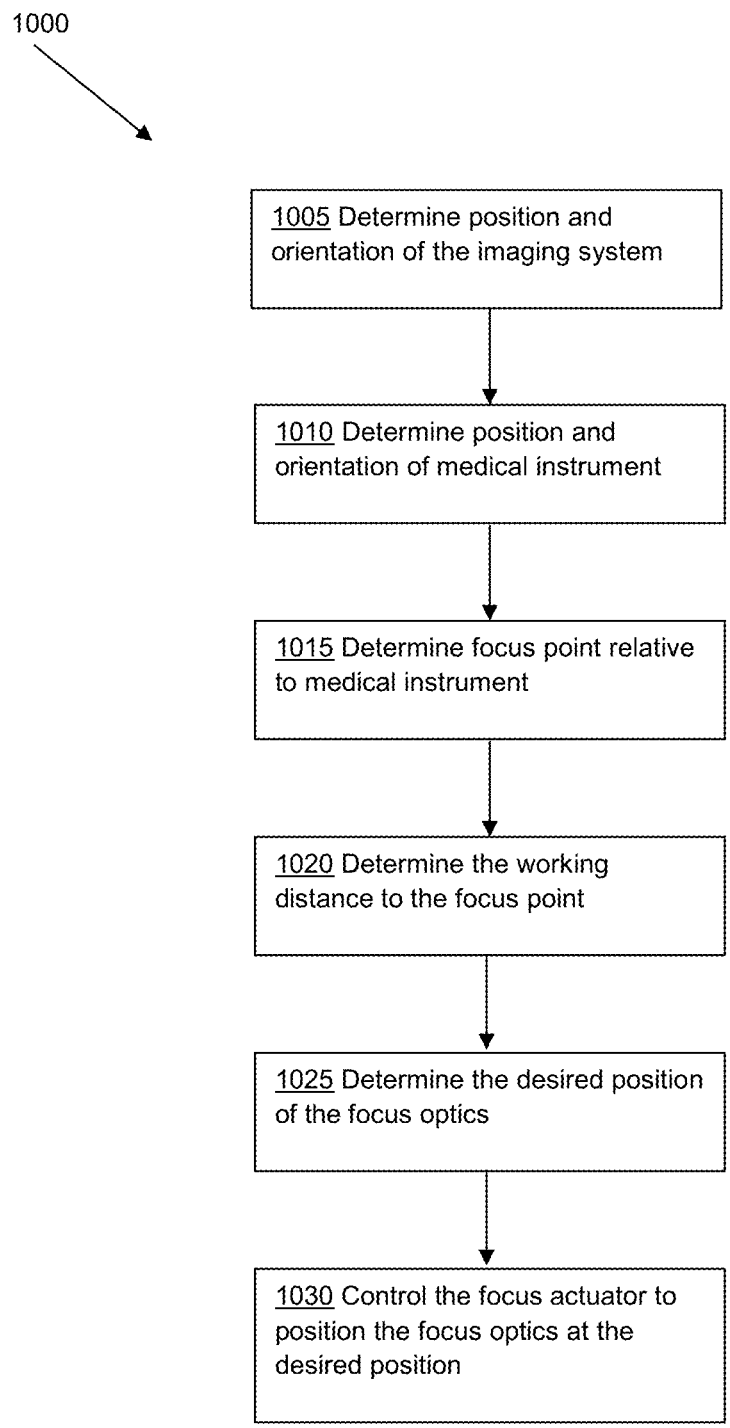
FIG. 10 is a flowchart illustrating an example method of autofocusing relative to a medical instrument, using an example optical imaging system.

Referring to FIG. 10, this flowchart illustrates an example method 1000 of autofocusing relative to a medical instrument during a medical procedure. The method 1000 may be performed using an example optical imaging system as disclosed herein. The method 1000 may be similar to the method 900. At step 1005, the position and orientation of the imaging system is determined. This may be done by tracking the imaging system, by performing calibration, or by tracking the positioning system on which the imaging system is mounted, for example. At step 1010, the position and orientation of the medical instrument is determined. This may be done by tracking the medical instrument, e.g., using a navigation system, by sensing the medical instrument, e.g., using an infrared or machine vision component of the imaging system, or by any other suitable methods. At step 1015, the focus point is determined relative to the medical instrument. Determining the focus point may include looking up preset definitions, e.g., stored in a database, of focus points for different medical instruments, and calculating the focus point for the particular medical instrument being used. At step 1020, the working distance between the imaging system and the focus point is determined. At step 1025, the desired position of the focus optics is determined, in order to achieve a focused image. At step 1030, the focus actuator is controlled, e.g., by a controller of the imaging system, to position the focus optics at the desired position. A focused image may then be captured, for example using a camera of the optical imaging system.

Referring back to FIGS. 9 and 10, the methods 900, 1000 may be entirely performed by the controller of the imaging system, or may be partly performed by the controller and partly performed by an external system. For example, one or more of: determining the position/orientation of the imaging system, determining the position/orientation of the imaging target or medical instrument, determining the working distance, or determining the desired position of the focus optics may be performed by one or more external systems. The controller of the imaging system may simply receive commands, from the external system(s) to position the focus optics at the desired position, or the controller of the imaging system may determine the desired position of the focus optics after receiving the calculated working distance from the external system(s).

Figure 12:
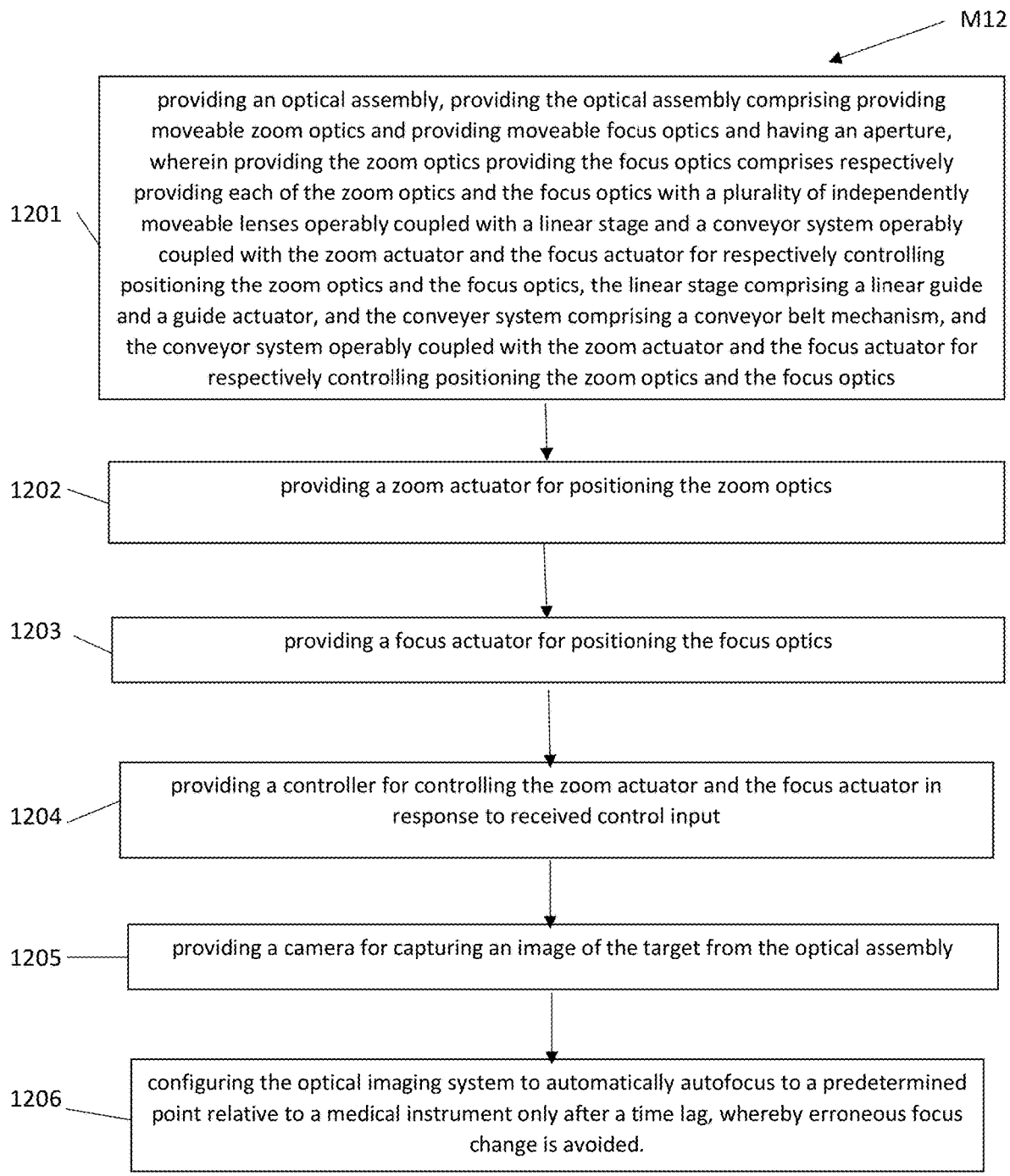
FIG. 12 is a flowchart illustrating a method of providing an optical imaging system for imaging a target during a medical procedure.

Referring to FIG. 12, a method M12 of providing an optical imaging system for imaging a target during a medical procedure, in accordance with an embodiment of the present disclosure. The method M12 comprises: providing an optical assembly, providing the optical assembly comprising providing moveable zoom optics and providing moveable focus optics and having an aperture, as indicated by block 1201; providing a zoom actuator for positioning the zoom optics, as indicated by block 1202; providing a focus actuator for positioning the focus optics, as indicated by block 1203; providing a controller for controlling the zoom actuator and the focus actuator in response to received control input, as indicated by block 1204; and providing a camera for capturing an image of the target from the optical assembly, as indicated by block 1205, wherein providing the zoom optics providing the focus optics comprises respectively providing each of the zoom optics and the focus optics with a plurality of independently moveable lenses operably coupled with a linear stage and a conveyer system operably coupled with the zoom actuator and the focus actuator for respectively controlling positioning the zoom optics and the focus optics, the linear stage comprising a linear guide and a guide actuator, and the conveyer system comprising a conveyor belt mechanism, and the conveyer system operably coupled with the zoom actuator and the focus actuator for respectively controlling positioning the zoom optics and the focus optics; and configuring the optical imaging system to automatically autofocus to a predetermined point relative to a medical instrument only after a time lag, whereby erroneous focus change is avoided, as indicated by block 1206.

While some embodiments or aspects of the present disclosure may be implemented in fully functioning computers and computer systems, other embodiments or aspects may be capable of being distributed as a computing product in a variety of forms and may be capable of being applied regardless of the particular type of machine or computer readable media used to actually effect the distribution. At least some aspects disclosed may be embodied, at least in part, in software. That is, some disclosed techniques and methods may be carried out in a computer system or other data processing system in response to its processor, such as a microprocessor, executing sequences of instructions contained in a memory, such as ROM, volatile RAM, non-volatile memory, cache or a remote storage device.

A computer readable storage medium may be used to store software and data which when executed by a data processing system causes the system to perform various methods or techniques of the present disclosure. The executable software and data may be stored in various places including for example ROM, volatile RAM, non-volatile memory and/or cache. Portions of this software and/or data may be stored in any one of these storage devices. Examples of computer-readable storage media may include, but are not limited to, recordable and non-recordable type media such as volatile and non-volatile memory devices, read only memory (ROM), random access memory (RAM), flash memory devices, floppy and other removable disks, magnetic disk storage media, optical storage media, e.g., compact discs (CDs), digital versatile disks (DVDs), etc., among others. The instructions can be embodied in digital and analog communication links for electrical, optical, acoustical or other forms of propagated signals, such as carrier waves, infrared signals, digital signals, and the like. The storage medium may be the internet cloud, or a computer readable storage medium such as a disc.

Furthermore, at least some of the methods described herein may be capable of being distributed in a computer program product comprising a computer readable medium that bears computer usable instructions for execution by one or more processors, to perform aspects of the methods described. The medium may be provided in various forms such as, but not limited to, one or more diskettes, compact disks, tapes, chips, USB keys, external hard drives, wire-line transmissions, satellite transmissions, internet transmissions or downloads, magnetic and electronic storage media, digital and analog signals, and the like. The computer useable instructions may also be in various forms, including compiled and non-compiled code.

At least some of the elements of the systems described herein may be implemented by software, or a combination of software and hardware. Elements of the system that are implemented via software may be written in a high-level procedural language such as object oriented programming or a scripting language. Accordingly, the program code may be written in C, C++, J++, or any other suitable programming language and may comprise modules or classes, as is known to those skilled in object oriented programming. At least some of the elements of the system that are implemented via software may be written in assembly language, machine language or firmware as needed. In either case, the program code can be stored on storage media or on a computer readable medium that is readable by a general or special purpose programmable computing device having a processor, an operating system and the associated hardware and software that is necessary to implement the functionality of at least one of the embodiments described herein. The program code, when read by the computing device, configures the computing device to operate in a new, specific and predefined manner in order to perform at least one of the methods described herein.

While the teachings described herein are in conjunction with various embodiments for illustrative purposes, it is not intended that the teachings be limited to such embodiments. On the contrary, the teachings described and illustrated herein encompass various alternatives, modifications, and equivalents, without departing from the described embodiments, the general scope of which is defined in the appended claims. Except to the extent necessary or inherent in the processes themselves, no particular order to steps or stages of methods or processes described in this disclosure is intended or implied. In many cases, the order of process steps may be varied without changing the purpose, effect, or import of the methods described.

What is claimed:

1. An intraoperative optical imaging system for imaging a target during a medical procedure, the intraoperative optical imaging system comprising:
  an optical assembly comprising at least one moveable zoom optic and at least one moveable focus optic and having an aperture;
  a zoom actuator for positioning the at least one moveable zoom optic;
  a focus actuator for positioning the at least one moveable focus optic;
  a controller for independently controlling the at least one moveable zoom optic and the at least one moveable focus optic by respectively using the zoom actuator and the focus actuator in response to received control input; and
  a camera for capturing an image of the target from the optical assembly,
  each of the at least one moveable zoom optic and the at least one moveable focus optic comprising at least one independently moveable lens operably coupled with a linear stage and a conveyer system operably coupled with the zoom actuator and the focus actuator for respectively controlling positioning the least one moveable zoom optic and the at least one moveable focus optic, the linear stage comprising a linear guide and a guide actuator, and the conveyer system comprising a conveyor belt mechanism, and the conveyer system operably coupled with the zoom actuator and the focus actuator for respectively controlling positioning the at least one moveable zoom optic and the at least one moveable focus optic,
  at least one of the zoom actuator and the focus actuator comprising at least one of a shape-changing material and a smart material, and
  the optical imaging system further configured to:
    automatically autofocus to a predetermined point relative to a medical instrument only after a time lag, whereby erroneous focus change is avoided;
    determine a working distance between an imaging target and the aperture;
    determine a desired position of the focus optics based on the working distance;
    position the focus optics at the desired position;
    receive information about position and orientation of the optical imaging system;
    using the received information to determine the working distance relative to the imaging target;
    determine there is no medical instrument with a focus point within a current field of view of the optical imaging system;
    perform autofocusing on another imaging target different other than the focus point;
    receive information about position and orientation of the medical instrument;
    determine position of the focus point based on the position and orientation of the medical instrument;
    determine the working distance using the determined position of the focus point;
    receive information about position and orientation of the positioning system;
    determine position and orientation of the optical imaging system using known position and orientation of the optical imaging system relative to the positioning system; and using the determined position and orientation of the optical imaging system to determine the working distance;
wherein the information about the position and orientation of the medical instrument, the positioning system and optical imaging system is received from an external navigation system;
wherein the optical imaging system is mounted on a positioning system,
wherein the imaging target is a focus point defined relative to a medical instrument.

2. The optical imaging system of claim 1,
wherein the aperture is adjustable,
wherein the optical imaging system is further configured to:
operate at a minimum working distance from the target, the minimum working distance defined between the aperture of the optical assembly and the target;
automatically change between different autofocus modes;
autofocus through a predefined depth range;
capture focused images at different depths through the predefined depth range;
mount in relation to a moveable support structure; and
one of automatically autofocus to a predetermined point relative to the medical instrument and automatically autofocus to a predetermined point relative to the medical instrument only if a focus point, relative to the medical instrument, is within a field of view of the optical imaging system, whereby unintentional focus change is avoided, and
wherein the controller is configured to:
determine the minimum working distance by receiving information from a navigation system external to the optical imaging system, the information comprising information relating to a position and an orientation of a positioning system and information relating to a position and an orientation of the medical instrument by using a machine vision component; and
determine a desired position of the focus optics based on the minimum working distance, and control the focus actuator to position the focus optics at the desired position.

3. The optical imaging system of claim 2, wherein the optical imaging system further comprises a support connector configured to removably mount the optical imaging system in relation to the moveable support structure.

4. The optical imaging system of claim 2, wherein the moveable support structure comprises at least one of: a robotic arm, a manually operated support arm, and a moveable support frame.

5. The optical imaging system of claim 2, further comprising a manual release button configured to enable manually positioning the optical imaging system.

6. The optical imaging system of claim 1, further comprising a single housing configured to accommodate at least one of: the optical assembly, the zoom actuator, the focus actuator, and the camera, wherein the housing is further configured to accommodate the controller.

7. The optical imaging system of claim 1, wherein the controller is configured to communicate with a processor, the controller responsive to control input received from the processor via a user interface.

8. The optical imaging system of claim 1, wherein the controller is configured to communicate with a processor, the controller responsive to control input received from the processor via an input system.

9. The optical imaging system of claim 1, further comprising a three-dimensional (3D) camera configured to capture 3D information of the target, wherein the 3D camera is configured to automatically focus through a predefined depth range and automatically capture a plurality of focused images corresponding to a plurality of depths through the depth range, wherein the imaging system is configured to generate a depth map based on the plurality of focused images corresponding to the plurality of depths through the depth range, wherein the depth map provides focused views of the field of view, corresponding to the plurality of depths through the depth range, and wherein the depth map comprises at least one of contours, color-coding, and any other indicator of each depth of the plurality of depths.

10. The optical imaging system of claim 1, further comprising at least one linear stage mechanism configured to move at least one of the zoom optics and focus optics.

11. The optical imaging system of claim 1, further comprising at least one of: a power source, a power connector configured to couple with the power source, and a light source configured to couple with the power source.

12. The optical imaging system of claim 1, further comprising an array of trackable markers configured to track position and orientation of the optical imaging system by the navigation system.

13. The optical imaging system of claim 2, wherein the minimum working distance comprises a range of approximately 15 cm to approximately 75 cm.

14. The optical imaging system of claim 1, wherein the information received from the navigation system comprises information relating to the position of the optical assembly relative to a position of the target.

15. The optical imaging system of claim 2, wherein the optical imaging system is supported by a positioning system, wherein the information received from the navigation system comprises information relating to the position of the positioning system relative to a position of the target, and wherein the minimum working distance is determined by using a known position of the optical assembly relative to the position of the positioning system.

16. The optical imaging system of claim 2, wherein the minimum working distance is determined as a distance between the aperture of the optical assembly and the target, the target being the focus point defined relative to the medical instrument having a known position and a known orientation, and wherein the information received from the navigation system comprises information relating to the known position and the known orientation of the medical instrument.

17. The optical imaging system of claim 1, further comprising at least one of:
a memory coupled with the controller, the memory configured to store image data captured by the camera; and
a wireless transceiver configured to transmit data from the optical imaging system
wherein at least one of the zoom actuator and the focus actuator further comprises at least one of an electric motor, an engine, a pneumatic actuator, a hydraulic actuator, and a piezoelectric material.

18. A method of providing an intraoperative optical imaging system for imaging a target during a medical procedure, the method comprising:
providing an optical assembly, providing the optical assembly comprising providing at least one moveable zoom optic and providing at least one moveable focus optic and having an aperture;

providing a zoom actuator for positioning the at least one moveable zoom optic;

providing a focus actuator for positioning the at least one moveable focus optic;

providing a controller for independently controlling the at least one moveable zoom optic and the at least one moveable focus optic by respectively using the zoom actuator and the focus actuator in response to received control input; and providing a camera for capturing an image of the target from the optical assembly, wherein providing the zoom optics providing the focus optics comprises respectively providing each of the at least one moveable zoom optic and the at least one focus optic with at least one independently moveable lens operably coupled with a linear stage and a conveyer system operably coupled with the zoom actuator and the focus actuator for respectively controlling positioning the at least one moveable zoom optic and the at least one focus optic, the linear stage comprising a linear guide and a guide actuator, and the conveyer system comprising a conveyor belt mechanism, and the conveyer system operably coupled with the zoom actuator and the focus actuator for respectively controlling positioning the at least one moveable zoom optic and the at least one focus optic, and wherein providing at least one of the zoom actuator and the focus actuator comprises providing at least one of a shape-changing material and a smart material; and configuring the optical imaging system to automatically autofocus to a predetermined point relative to a medical instrument only after a time lag, whereby erroneous focus change is avoided;

receiving information about position and orientation of the optical imaging system;

using the received information to determine the working distance relative to the imaging target;

determining there is no medical instrument with a focus point within a current field of view of the optical imaging system;

performing autofocusing on another imaging target different other than the focus point;

receiving information about position and orientation of the medical instrument;

determining position of the focus point based on the position and orientation of the medical instrument;

determining the working distance using the determined position of the focus point;

receiving information about position and orientation of the positioning system;

determining position and orientation of the optical imaging system using known position and orientation of the optical imaging system relative to the positioning system; and using the determined position and orientation of the optical imaging system to determine the working distance, wherein the information about the position and orientation of the medical instrument, the positioning system and optical imaging system is received from an external navigation system;

wherein the optical imaging system is mounted on a positioning system; and wherein the imaging target is a focus point defined relative to a medical instrument.

19. A method of autofocusing using an intraoperative optical imaging system during a medical procedure, the method comprising:

providing an intraoperative optical imaging system for imaging a target during a medical procedure, providing the intraoperative optical imaging system comprising:

providing an optical assembly, providing the optical assembly comprising providing at least one moveable zoom optic and providing at least one moveable focus optic and having an aperture;

providing a zoom actuator for positioning the at least one moveable zoom optic;

providing a focus actuator for positioning the at least one moveable focus optic;

providing a controller for independently controlling the at least one moveable zoom optic and the at least one moveable focus optic by respectively using the zoom actuator and the focus actuator in response to received control input; and providing a camera for capturing an image of the target from the optical assembly, wherein providing the zoom optics providing the focus optics comprises respectively providing each of the at least one moveable zoom optic and the at least one focus optic with at least one independently moveable lens operably coupled with a linear stage and a conveyer system operably coupled with the zoom actuator and the focus actuator for respectively controlling positioning the at least one moveable zoom optic and the at least one focus optic, the linear stage comprising a linear guide and a guide actuator, and the conveyer system comprising a conveyor belt mechanism, and the conveyer system operably coupled with the zoom actuator and the focus actuator for respectively controlling positioning the at least one moveable zoom optic and the at least one focus optic, and wherein providing at least one of the zoom actuator and the focus actuator comprises providing at least one of a shape-changing material and a smart material; and configuring the optical imaging system to automatically autofocus to a predetermined point relative to a medical instrument only after a time lag, whereby erroneous focus change is avoided;

determining a working distance between an imaging target and the aperture;

determining a desired position of the focus optics based on the working distance;

positioning the focus optics at the desired position;

receiving information about position and orientation of the optical imaging system;

using the received information to determine the working distance relative to the imaging target;

determining there is no medical instrument with a focus point within a current field of view of the optical imaging system;

performing autofocusing on another imaging target different other than the focus point;

receiving information about position and orientation of the medical instrument;

determining position of the focus point based on the position and orientation of the medical instrument;

determining the working distance using the determined position of the focus point;

receiving information about position and orientation of the positioning system;

determining position and orientation of the optical imaging system using known position and orientation of the optical imaging system relative to the positioning system; and using the determined position and orientation of the optical imaging system to determine the working distance;

wherein the information about the position and orientation of the medical instrument, the positioning system and optical imaging system is received from an external navigation system;

wherein the optical imaging system is mounted on a positioning system, wherein the imaging target is a focus point defined relative to a medical instrument.

* * * * *